United States Patent
Sato

(10) Patent No.: US 10,422,890 B2
(45) Date of Patent: Sep. 24, 2019

(54) RADIATION IMAGING APPARATUS, CONTROL METHOD OF RADIATION IMAGING APPARATUS, AND RADIATION IMAGING SYSTEM

(71) Applicant: CANON KABUSHIKI KAISHA, Tokyo (JP)

(72) Inventor: Kanako Sato, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/398,917

(22) Filed: Jan. 5, 2017

(65) Prior Publication Data
US 2017/0212252 A1 Jul. 27, 2017

(30) Foreign Application Priority Data
Jan. 22, 2016 (JP) ................. 2016-010870

(51) Int. Cl.
| | |
|---|---|
| G01T 1/20 | (2006.01) |
| G01N 23/04 | (2018.01) |
| G01T 1/24 | (2006.01) |
| H04N 5/32 | (2006.01) |
| H04N 5/3745 | (2011.01) |

(52) U.S. Cl.
CPC ........... *G01T 1/2018* (2013.01); *G01N 23/04* (2013.01); *G01T 1/247* (2013.01); *H04N 5/32* (2013.01); *H04N 5/37452* (2013.01)

(58) Field of Classification Search
CPC ....... G01T 1/2018; G01T 1/247; G01N 23/04; H04N 5/32; H04N 5/37452
See application file for complete search history.

(56) References Cited

U.S. PATENT DOCUMENTS

| | | | |
|---|---|---|---|
| 2004/0146192 A1* | 7/2004 | Langan | A61B 6/4233 382/132 |
| 2008/0217544 A1* | 9/2008 | Sato | G01T 1/247 250/370.08 |
| 2011/0205100 A1* | 8/2011 | Bogaerts | H04N 5/3575 341/169 |
| 2017/0094113 A1* | 3/2017 | Togashi | H03M 1/1245 |

FOREIGN PATENT DOCUMENTS

| | | |
|---|---|---|
| JP | 2010-541101 | 12/2010 |
| JP | 2014-030130 | 2/2014 |
| WO | WO 2009/045904 A | 4/2009 |

* cited by examiner

Primary Examiner — Christine S. Kim
(74) Attorney, Agent, or Firm — Venable LLP

(57) ABSTRACT

A radiation imaging apparatus includes an imaging unit having sensors configured to detect radiation, and configured to output an analog signal from each sensor, an AD converter configured to, in each AD conversion period corresponding to a frame, convert the analog signals from the imaging unit into digital signals and output the digital signals as a serial data string of bits, a serial-parallel conversion unit configured to convert, into parallel data, the serial data string of the bits from the AD converter, and an alignment unit configured to perform alignment for the serial-parallel conversion unit to identify the serial data string. The alignment unit performs the alignment in at least a period between one AD conversion period and another analog-to-digital conversion period, in addition to performing the alignment before a first AD conversion period.

18 Claims, 20 Drawing Sheets

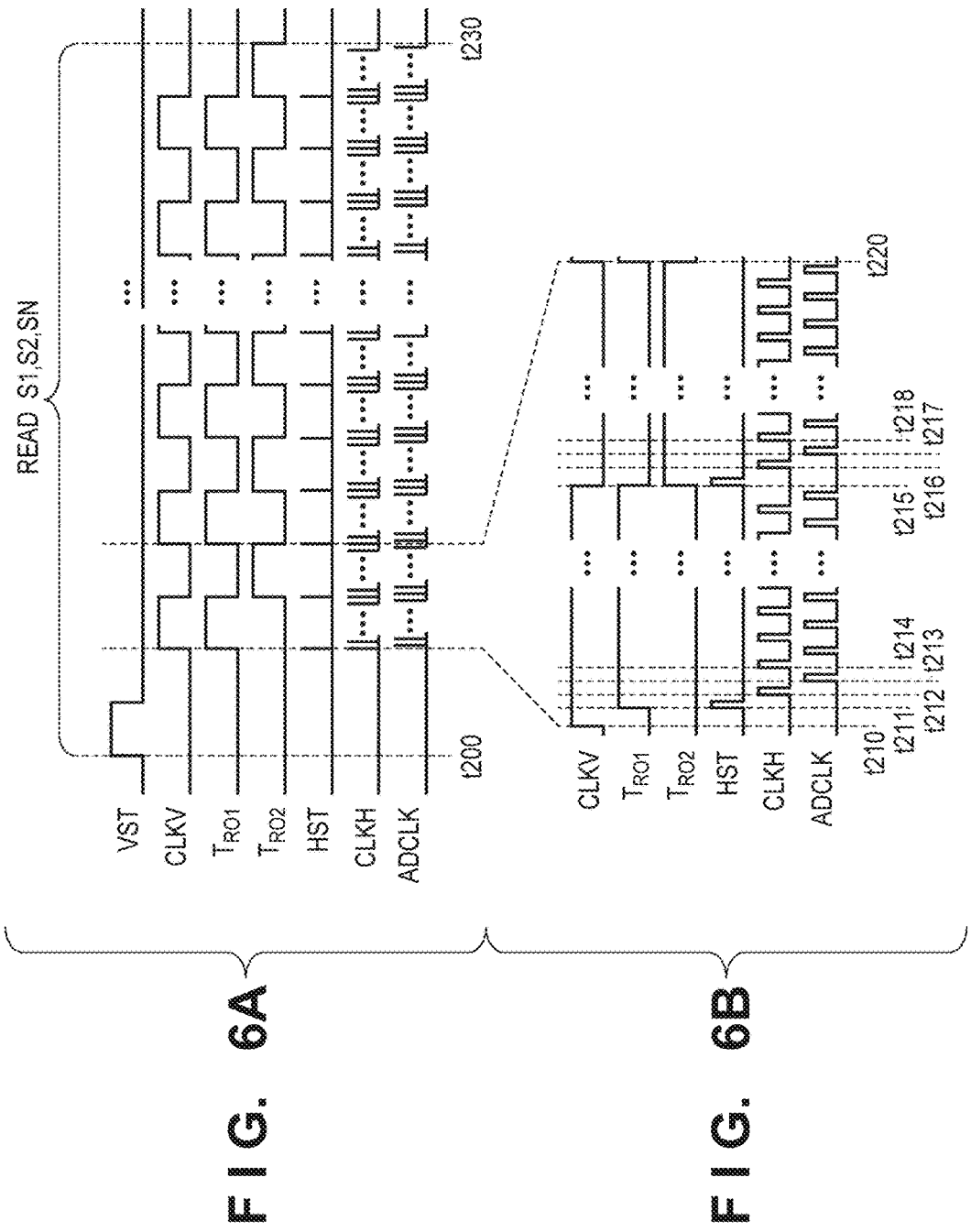

F I G. 20
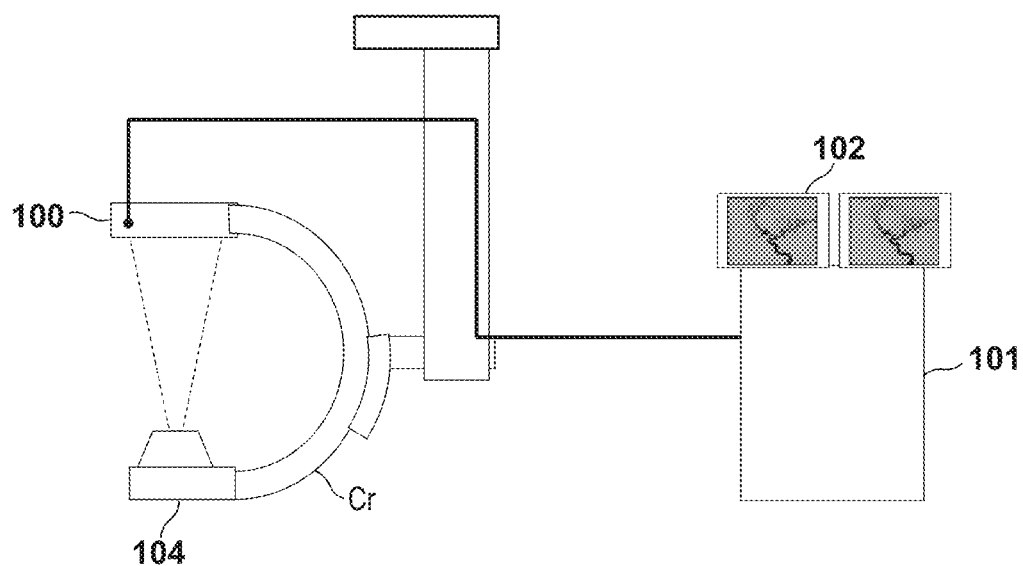

RADIATION IMAGING APPARATUS, CONTROL METHOD OF RADIATION IMAGING APPARATUS, AND RADIATION IMAGING SYSTEM

BACKGROUND OF THE INVENTION

Field of the Invention

The present invention relates to a radiation imaging apparatus, a control method of the radiation imaging apparatus, and a radiation imaging system.

Description of the Related Art

A radiation imaging apparatus is known in which a plurality of sensors or pixels detecting radiation are arrayed two-dimensionally. A radiation imaging apparatus described in Japanese Patent Laid-Open No. 2014-030130 includes a scintillator, a flat panel sensor which detects light from the scintillator, an analog-to-digital converter which performs analog-to-digital conversion on a signal from the flat panel sensor, and an image processing unit which processes a digital signal from the analog-to-digital converter.

In the radiation imaging apparatus described in Japanese Patent Laid-Open No. 2014-030130, for example, serial data transmission can be adopted to transmit the digital signal from the analog-to-digital converter to the image processing unit. In serial data transmission, a header can be added to serial data in order to detect a data break (for example, Japanese Patent Laid-Open No. 2010-541101). If a header is added to data to be transmitted, however, a delay occurs in data transmission accordingly.

On the other hand, there is also considered a method of continuing to convert transferred serial data into parallel data without providing a header. In this case, it is only necessary to perform alignment just once before starting to transfer serial data. With such a method, however, if a bit shift occurs due to the influence of noise such as static electricity during a capturing operation, it is impossible to recover from that state.

SUMMARY OF THE INVENTION

The present provides a technique advantageous in allowing recovery, when a bit shift occurs, from a state having the bit shift, while suppressing a delay in data transmission.

One of features of the present invention provides radiation imaging apparatus which captures radiation images of a plurality of frames successively, the apparatus comprising: an imaging unit having a plurality of sensors configured to detect radiation, and configured to output an analog signal from each of the plurality of sensors; an analog-to-digital converter configured to, in each of a plurality of analog-to-digital conversion periods corresponding to the plurality of frames, convert the individual analog signals from the imaging unit into individual digital signals and output the individual digital signals as a serial data string of a plurality of bits; a serial-parallel conversion unit configured to convert, into parallel data, the serial data string of the plurality of bits transmitted from the analog-to-digital converter via a transmission path; and an alignment unit configured to perform alignment for the serial-parallel conversion unit to identify the serial data string of the plurality of bits, wherein the alignment unit performs the alignment in at least a period between, out of the plurality of analog-to-digital conversion periods, one analog-to-digital conversion period and another analog-to-digital conversion period, in addition to performing the alignment before a first analog-to-digital conversion period out of the plurality of analog-to-digital conversion periods.

Further features of the present invention will become apparent from the following description of exemplary embodiments with reference to the attached drawings.

BRIEF DESCRIPTION OF THE DRAWINGS

FIGS. 6A and 6B are timing charts exemplifying the operation of the radiation imaging apparatus according to the embodiment;

FIG. 20 is a view showing an application example of the radiation imaging system according to the embodiment.

DESCRIPTION OF THE EMBODIMENTS

An exemplary embodiment of the present invention will be described below with reference to the accompanying drawings.

Figure 1:
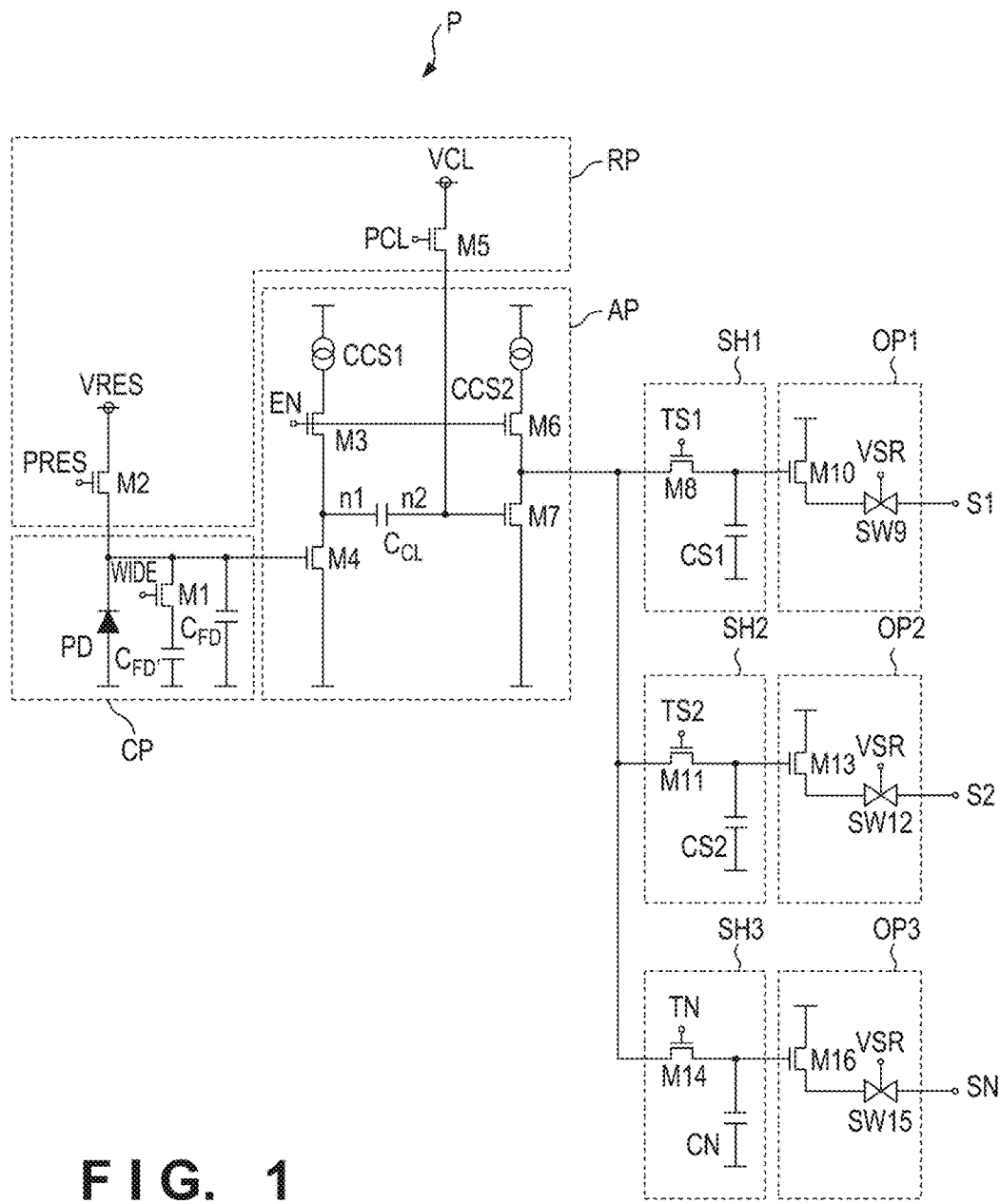
FIG. 1 is a circuit diagram showing the arrangement of a pixel of a radiation imaging apparatus according to an embodiment.
Figure 2:
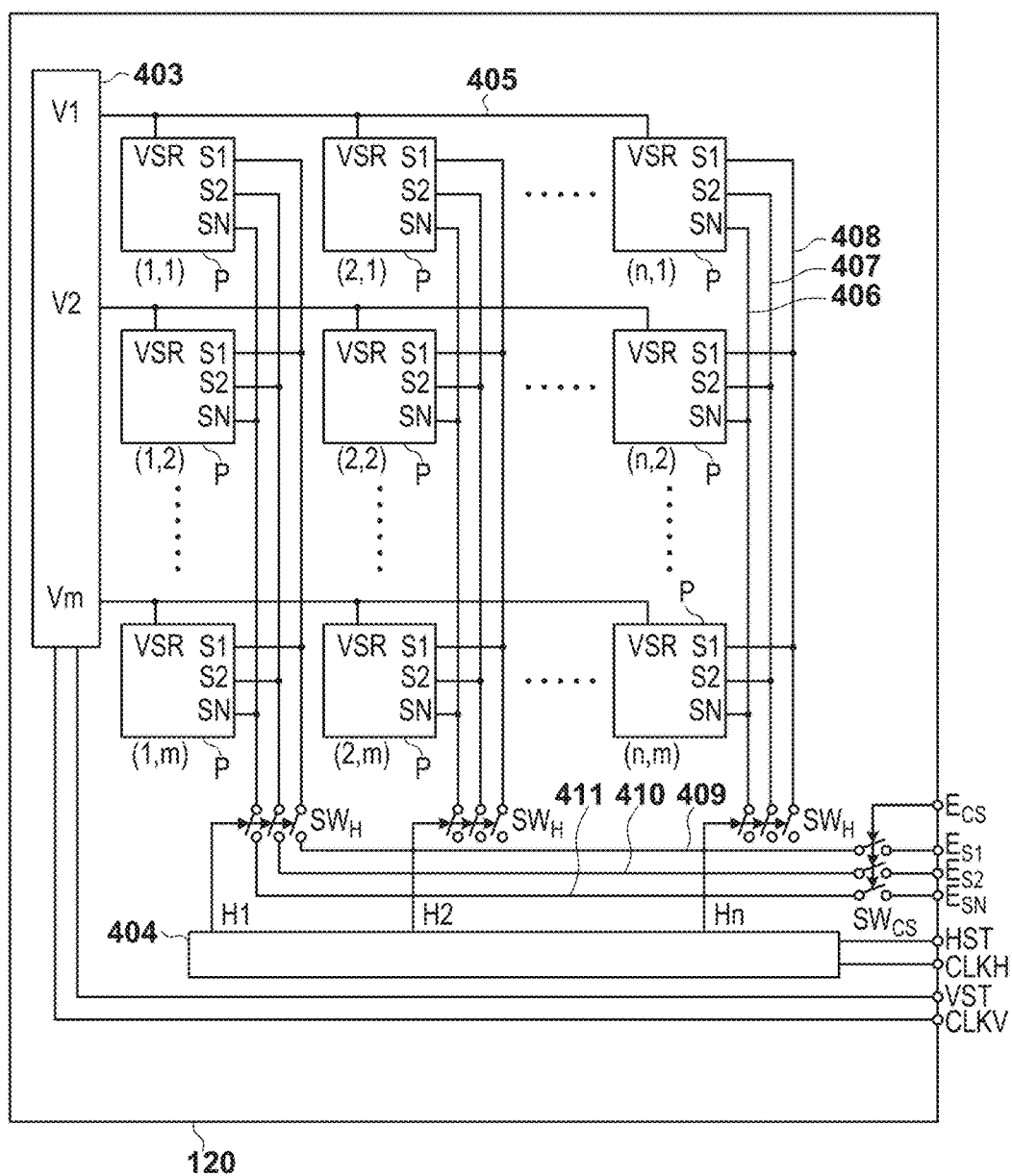
FIG. 2 is a diagram showing the arrangement of an imaging block of the radiation imaging apparatus according to the embodiment.
Figure 3:
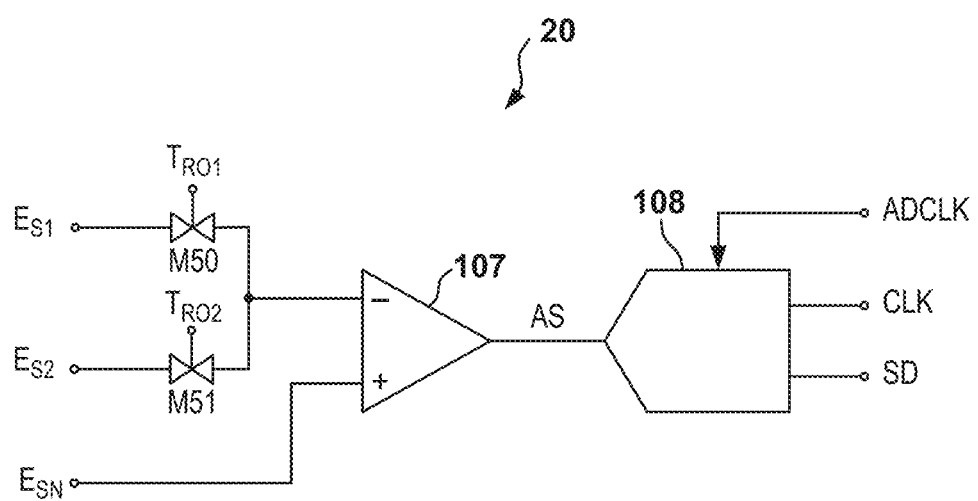
FIG. 3 is a view showing a readout circuit of the radiation imaging apparatus according to the embodiment.
Figure 4:
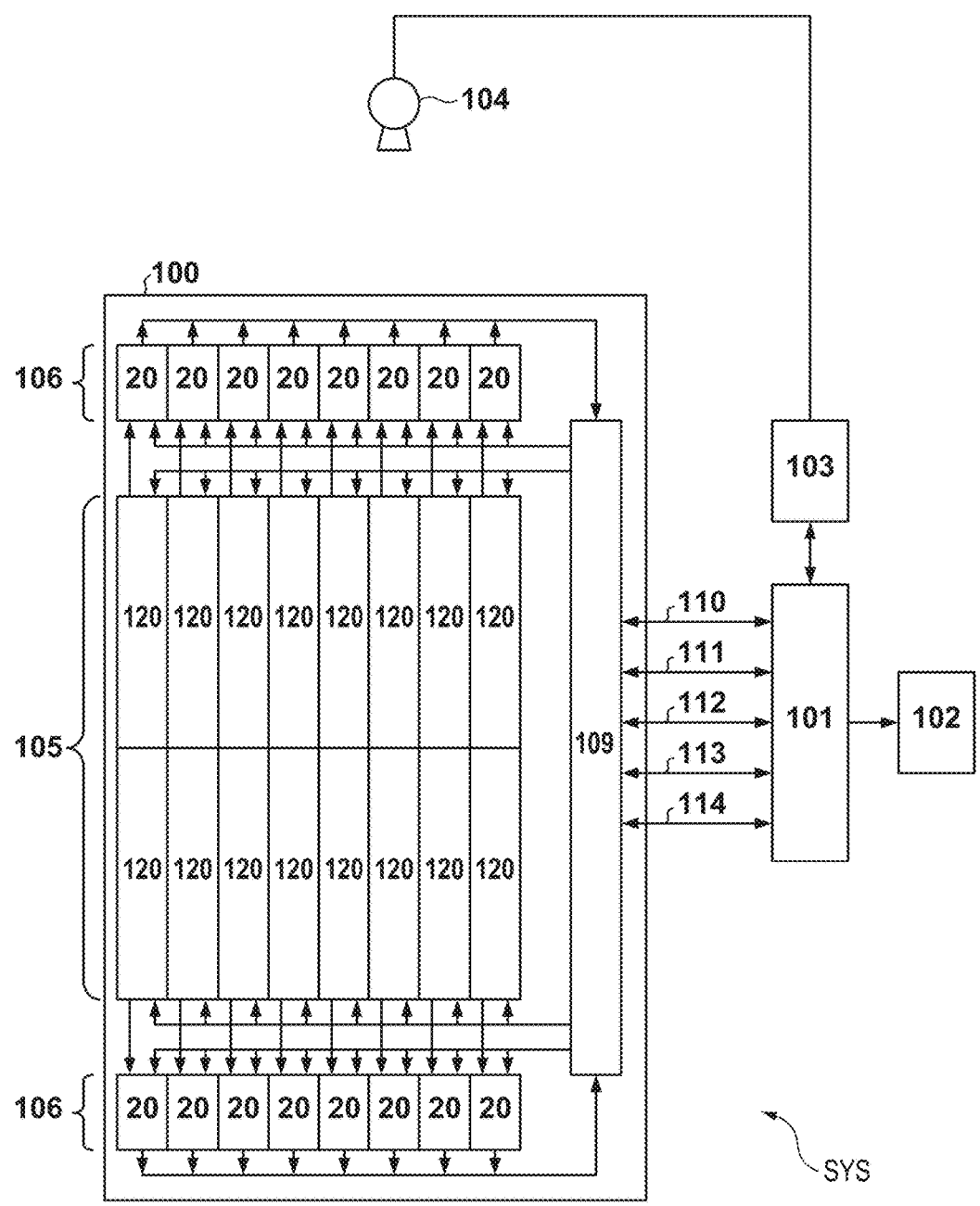
FIG. 4 is a diagram showing the arrangement of a radiation imaging system according to the embodiment.

FIG. 4 is a diagram showing the arrangement of a radiation imaging system SYS according to an embodiment of the present invention. The radiation imaging system SYS can include a radiation imaging apparatus 100, a processing unit 101, a display unit 102, an exposure control unit 103, and a radiation source 104. The radiation imaging apparatus 100 can include an imaging unit 105, readout units 106, and a control unit 109. The imaging unit 105 can include a plurality of imaging blocks 120. The readout units 106 can include a plurality of readout circuits 20 which read out signals from the plurality of imaging blocks 120, respectively. FIG. 2 is a diagram showing the arrangement of one imaging block 120. FIG. 1 is a circuit diagram showing the arrangement of one pixel P out of the plurality of pixels P in the imaging blocks 120 or the imaging unit 105. FIG. 3 is a view showing the arrangement of one readout circuit 20.

The arrangement of the pixel P will be described with reference to FIG. 1. The pixel P is a sensor which detects radiation. Although not shown in FIG. 1, the imaging block 120 or the imaging unit 105 can include a scintillator (wavelength conversion member) which converts the radiation into light. The scintillator can be shared by the plurality of pixels P. The pixel P can include a conversion unit CP, an amplification unit AP, a reset unit RP, a first holding unit SH1, a second holding unit SH2, a third holding unit SH3, a first output unit OP1, a second output unit OP2, and a third output unit OP3. The conversion unit CP can include a photodiode PD, a transistor M1, a floating diffusion capacitor $C_{FD}$ (to be referred to as the FD capacitor $C_{FD}$ hereinafter), and an additional capacitor $C_{FD}'$ configured to switch sensitivity. The photodiode PD is a photoelectric conversion element and converts, in accordance with emitted radiation, the light generated by the scintillator into charges. Note that the photodiode (photoelectric conversion element) PD may be configured to convert the radiation into charges directly. In this case, the scintillator is not needed.

The FD capacitor $C_{FD}$ converts the charges generated in photoelectric conversion by the photodiode PD into a voltage. This voltage is provided to the amplification unit AP. The capacitor $C_{FD}'$ is used to switch the sensitivity of the pixel P to the radiation and is connected to the photodiode PD via a transistor M1 (switch element). The transistor M1 is set in a conductive state by activating a signal WIDE, and the FD capacitor $C_{FD}$ and the capacitor $C_{FD}'$ are connected in parallel, increasing a capacitance value. This changes a conversion coefficient, that is, sensitivity obtained when the charges generated in photoelectric conversion by the photodiode PD are converted into the voltage. By controlling conduction/nonconduction of the transistor M1, it is possible to provide, to the amplification unit AP, the first signal serving as a voltage corresponding to charges converted by the conversion unit CP of the first sensitivity and the second signal serving as a voltage corresponding to charges converted by a conversion unit of the second sensitivity different from the first sensitivity.

The amplification unit AP can include a first control transistor M3, a first amplification transistor M4, a clamp capacitor $C_{CL}$, a second control transistor M6, a second amplification transistor M7, and two constant current sources CCS1 and CCS2. The first control transistor M3, the first amplification transistor M4, and the constant current source CCS1 are connected in series so as to form one current path. The first amplification transistor M4 which receives the voltage from the conversion unit CP is set in an operating state by activating an enable signal EN supplied to the gate of the first control transistor M3. A source follower circuit is thus formed, and a voltage obtained by amplifying the voltage from the conversion unit CP is output from the first amplification transistor M4. The voltage output from the first amplification transistor M4 is supplied to the second amplification transistor M7 via the clamp capacitor $C_{CL}$.

The second control transistor M6, the second amplification transistor M7, and the constant current source CCS2 are connected in series so as to form one current path. The first amplification transistor M4 which receives the voltage from the first amplification transistor M4 is set in the operating state by activating the enable signal EN supplied to the gate of the second control transistor M6. A source follower circuit is thus formed, and a voltage obtained by amplifying the voltage from the first amplification transistor M4 is output from the second amplification transistor M7. The clamp capacitor $C_{CL}$ is arranged in series between the first amplification transistor M4 and the second amplification transistor M7. A clamp operation by the clamp capacitor $C_{CL}$ will be described together with the reset unit RP to be described later.

The reset unit RP includes a first reset transistor M2 and a second reset transistor M5. Activating a signal PRES in the first reset transistor M2 will supply a predetermined voltage to the photodiode PD to initialize the charges of the photodiode PD and reset the voltage output to the amplification unit AP. The second reset transistor M5 resets the voltage output from the second amplification transistor M7 by supplying a predetermined voltage to a connection node between the clamp capacitor $C_{CL}$ and the second amplification transistor M7. A voltage corresponding to the voltage from the conversion unit CP at the time of reset by the first reset transistor M2 is supplied to a terminal n1 of the clamp capacitor $C_{CL}$. The second reset transistor M5 is set in the conductive state by activating a clamp signal PCL, and a clamp voltage VCL serving as a predetermined voltage is supplied to a terminal n2 of the clamp capacitor $C_{CL}$. In this manner, a potential difference generated between the two terminals n1 and n2 of the clamp capacitor $C_{CL}$ is clamped as a noise component. Thereafter, a change in voltage accompanying generation and accumulation of the charges in the photodiode PD is output as a signal component. This is the clamp operation using the clamp capacitor $C_{CL}$. The clamp operation suppresses kTC noise generated by the conversion unit CP and a noise component such as an offset of the first amplification transistor M4.

The first holding unit SH1 is a sample-and-hold circuit which samples and holds the first signal obtained by amplifying, by the amplification unit AP, the charges converted by the conversion unit CP of the first sensitivity. The first holding unit SH1 can include a first transfer transistor M8 and a first holding capacitor CS1. The first signal obtained by amplifying, by the amplification unit AP, a voltage corresponding to the charges converted by the conversion unit CP of the first sensitivity is transferred to and held by the capacitor CS1 when a control signal TS1 switches the state (the conductive state or the nonconductive state) of the first transfer transistor M8. The first output unit OP1 can include a first signal amplification transistor M10 and a first output switch SW9. The first signal amplification transistor M10 is a transistor configured to output a signal obtained by amplifying the voltage held by the first holding capacitor CS1. The first output switch SW9 transfers the signal output from the first signal amplification transistor M10. A constant current source (not shown) at the subsequent stage and the first signal amplification transistor M10 form a source follower circuit when a control signal VSR supplied to the first output switch SW9 sets the first output switch SW9 in the conductive state. Through such an operation, the first output unit OP1 outputs the first output signal corresponding to the first signal held by the first holding capacitor CS1.

The second holding unit SH2 is a sample-and-hold circuit which samples and holds the second signal obtained by amplifying, by the amplification unit AP, the charges converted by the conversion unit CP of the second sensitivity different from the first sensitivity. The second holding unit SH2 can include a second transfer transistor M11 and a second holding capacitor CS2. The second signal obtained by amplifying, by the amplification unit AP, a voltage corresponding to the charges converted by the conversion unit CP of the second sensitivity is transferred to and held by the capacitor CS2 when a control signal TS2 switches the state (the conductive state or the nonconductive state) of the second transfer transistor M11. The second output unit OP2 can include a second signal amplification transistor M13 and a second output switch SW12. The second signal amplification transistor M13 is a transistor configured to output a signal obtained by amplifying the voltage held by the second holding capacitor CS2. The second output switch SW12 transfers the signal output from the second signal amplification transistor M13. A constant current source (not shown) at the subsequent stage and the second signal amplification transistor M13 form a source follower circuit when the control signal VSR supplied to the second output switch SW12 sets the second output switch SW12 in the conductive state. Through such an operation, the second output unit OP2 outputs the second output signal corresponding to the second signal held by the second holding capacitor CS2.

The third holding unit SH3 is a sample-and-hold circuit which samples and holds an offset signal of the amplification unit AP. The third holding unit SH3 can include a third transfer transistor M14 and a third holding capacitor CN. The offset signal of the amplification unit AP is transferred to and held by the capacitor CN when a control signal TN switches the state (the conductive state or the nonconductive state) of the third transfer transistor M14. The third output unit OP3 can include a third signal amplification transistor M16 and a third output switch SW15. The third signal amplification transistor M16 is a transistor configured to output a signal obtained by amplifying the voltage held by the third holding capacitor CN. The third output switch SW15 transfers the signal output from the third signal amplification transistor M16. A constant current source (not shown) at the subsequent stage and the third signal amplification transistor M16 form a source follower circuit when the control signal VSR supplied to the third output switch SW15 sets the third output switch SW15 in the conductive state. Through such an operation, the third output unit OP3 outputs, from the pixel P, the third output signal based on the offset signal.

As shown in FIG. 2, the imaging block 120 includes an array in which the plurality of pixels P are arrayed so as to form a plurality (m) of rows and a plurality (n) of columns. The imaging block 120 can include the plurality of pixels P, a vertical scanning circuit (row selecting unit) 403 configured to select the plurality of pixels P on the row basis, and a horizontal scanning circuit (column selecting unit) 404 which selects a column on the row selected by the vertical scanning circuit 403. For example, each of the vertical scanning circuit 403 and the horizontal scanning circuit 404 is formed by a shift register and operates based on a control signal from the control unit 109. The vertical scanning circuit 403 supplies the control signals VSR to the plurality of pixels P via control lines 405 and selects the plurality of pixels P on the row basis based on the control signals VSR. The operating frequency of the row selecting unit (vertical scanning circuit 403) is higher than that of the column selecting unit (horizontal scanning circuit 404). That is, the row selecting unit (vertical scanning circuit 403) is slower than the column selecting unit (horizontal scanning circuit 404) in operation.

The imaging block 120 includes a terminal $E_{S1}$ for reading out the first signal held by the capacitor CS1 of each pixel P, a terminal $E_{S2}$ for reading out the second signal held by the capacitor CS2 of each pixel P, and a terminal $E_{SN}$ for reading out the voltage held by the capacitor CN of each pixel P. The imaging block 120 further includes a select terminal $E_{CS}$. Activating a signal received by the terminal $E_{CS}$ can read out the signal from each pixel P in the imaging block 120 via the terminals $E_{S1}$, $E_{S2}$, and $E_{SN}$.

Terminals S1, S2, and SN of each pixel P are connected to column signal lines 406 to 408 corresponding to the respective terminals. The column signal lines 406 to 408 are connected to analog output lines 409 to 411 via switches $SW_H$ which are set in the conductive state in response to a control signal from the horizontal scanning circuit 404. Signals of the analog output lines 409 to 411 are output from the terminals $E_{S1}$, $E_{S2}$, and $E_{SN}$ via a switch $SW_{CS}$ which is set in the conductive state in response to the signal received by the terminal $E_{CS}$.

The imaging block 120 further includes terminals HST, CLKH, VST, and CLKV each receiving, from the control unit 109, a control signal for controlling the vertical scanning circuit 403 and the horizontal scanning circuit 404. The terminal HST receives, from the control unit 109, the start pulse HST supplied to the horizontal scanning circuit 404. The terminal CLKH receives, from the control unit 109, the clock signal CLKH supplied to the horizontal scanning circuit 404. The terminal VST receives, from the control unit 109, the start pulse VST supplied to the vertical scanning circuit 403. The terminal CLKV receives, from the control unit 109, the clock signal CLKV supplied to the vertical scanning circuit 403. Based on the supplied start pulse HST and clock signal CLKH, the horizontal scanning circuit 404 generates and outputs a control signal H1 to Hn. Based on the supplied start pulse VST and clock signal CLKV, the vertical scanning circuit 403 generates and outputs the control signals V1 to Vm. Consequently, the first signal or the first output signal, the second output signal, and the third output signal are read out sequentially from each pixel by an X-Y addressing.

The arrangement of each of the plurality of readout circuits 20 which constitute the readout units 106 will now be described with reference to FIG. 3. Note that one readout circuit 20 can read out a signal from one imaging block 120. FIG. 3 shows one readout circuit 20. The readout circuit 20 can include, for example, a signal amplification unit 107 including a differential amplifier or the like and an analog-to-digital converter 108 which performs analog-to-digital conversion. The signal from the terminal $E_{S1}$ is supplied to an inverting input terminal of the signal amplification unit 107 via a switch M50 which is set in the conductive state in response to a control signal supplied from the control unit 109 to a terminal $T_{RO1}$. The signal from the terminal $E_{S2}$ is supplied to the inverting input terminal of the signal amplification unit 107 via a switch M51 which is set in the conductive state in response to a control signal supplied from the control unit 109 to a terminal $T_{RO2}$. The switches M50 and M51 are controlled so as to supply the signal of one of the terminal $E_{S1}$ and the terminal $E_{S2}$ to the inverting input terminal. Note that the switches M50 and M51, and the signal amplification unit 107 are designed to have a response characteristic capable of following the cycle of a signal ADCLK.

The signal from the terminal $E_{SN}$ is input to a non-inverting input terminal of the signal amplification unit 107. The signal amplification unit 107 amplifies the difference between the signal from the terminal $E_{S1}$ and the signal from the terminal $E_{SN}$ or the difference between the signal from the terminal $E_{S2}$ and the signal from the terminal $E_{SN}$ to generate an analog signal (analog image signal) AS, and outputs the signal. The analog-to-digital converter 108 performs analog-to-digital conversion on the analog signal AS output from the signal amplification unit 107 in accordance with the clock signal ADCLK supplied via an ADCLK terminal and outputs a conversion result as serial data SD. Note that the analog signal AS serving as the signal of one pixel P output from the signal amplification unit 107 is expressed as a serial data string of a plurality of bits in the format of the serial data SD. That is, the analog signal AS serving as the signal of one pixel P corresponds to the serial data string of the plurality of bits.

The arrangement of each of the radiation imaging apparatus 100 and the radiation imaging system SYS will now be described with reference to FIG. 4. As described above, the radiation imaging system SYS can include the radiation imaging apparatus 100, the processing unit 101, the display unit 102, the exposure control unit 103, and the radiation source 104. When a radiation image is captured, the processing unit 101 can perform synchronization control on the radiation imaging apparatus 100 and the exposure control unit 103. The radiation imaging apparatus 100 detects radiation (for example, X-rays, α-rays, β-rays, γ-rays, or the like) passing through a subject to be examined, a predetermined process is performed in the processing unit 101 or the like, and then image data based on the radiation is generated. The image data is displayed as the radiation image data on the display unit 102.

As exemplified in FIG. 4, the imaging unit 105 can be formed by arraying the plurality of imaging blocks 120 one-dimensionally or two-dimensionally. However, the imaging unit 105 may be formed by the single imaging block 120. A method of forming the imaging unit 105 by arraying the plurality of imaging blocks 120 one-dimensionally or two-dimensionally is advantageous in obtaining the large imaging unit 105. The imaging unit 105 includes the plurality of pixels (sensors) P which detect radiation and outputs an analog signal from each of the plurality of pixels P.

The control unit 109 of the radiation imaging apparatus 100 communicates control commands and synchronization signals with, for example, the processing unit 101, and outputs image data to the processing unit 101. The control unit 109 also controls the imaging unit 105 and the readout units 106. The control unit 109 uses image data (digital data) of the imaging blocks 120 that has undergone analog-to-digital conversion by the analog-to-digital converters 108 of the respective readout circuits 20 which form the readout units 106 to generate one frame data and outputs the data to the processing unit 101.

The control unit 109 and the processing unit 101 exchange control commands, control signals, and image data with each other via various types of interfaces. The processing unit 101 outputs setting information such as an operation mode and various types of parameters and imaging information to the control unit 109 via a control interface 110. In addition, the control unit 109 outputs apparatus information such as the operating state of the radiation imaging apparatus 100 to the processing unit 101 via the control interface 110. The control unit 109 also outputs the image data obtained by the radiation imaging apparatus 100 to the processing unit 101 via an image data interface 111. In addition, the control unit 109 notifies the processing unit 101, by using a READY signal 112, that the radiation imaging apparatus 100 is ready for imaging. In response to the READY signal 112 from the control unit 109, the processing unit 101 notifies the control unit 109 of the irradiation start (exposure) timing of radiation by using an external synchronization signal 113. The control unit 109 also starts radiation irradiation by outputting a control signal to the exposure control unit 103 while an exposure permission signal 114 is in an enabled state.

The radiation imaging apparatus 100 can have an operation mode of obtaining signals with, for example, two sensitivities in each pixel and generating image data by using the signals (for example, an operation mode of performing dynamic range expansion). As one method of implementing this operation mode, there is a method of holding the first signal obtained with the first sensitivity and the second signal obtained with the second sensitivity in the first holding unit SH1 and the second holding unit SH2, respectively, of each pixel P and individually reading out the signals, and combining the read out signals of the respective sensitivities for each pixel.

Figure 5A:
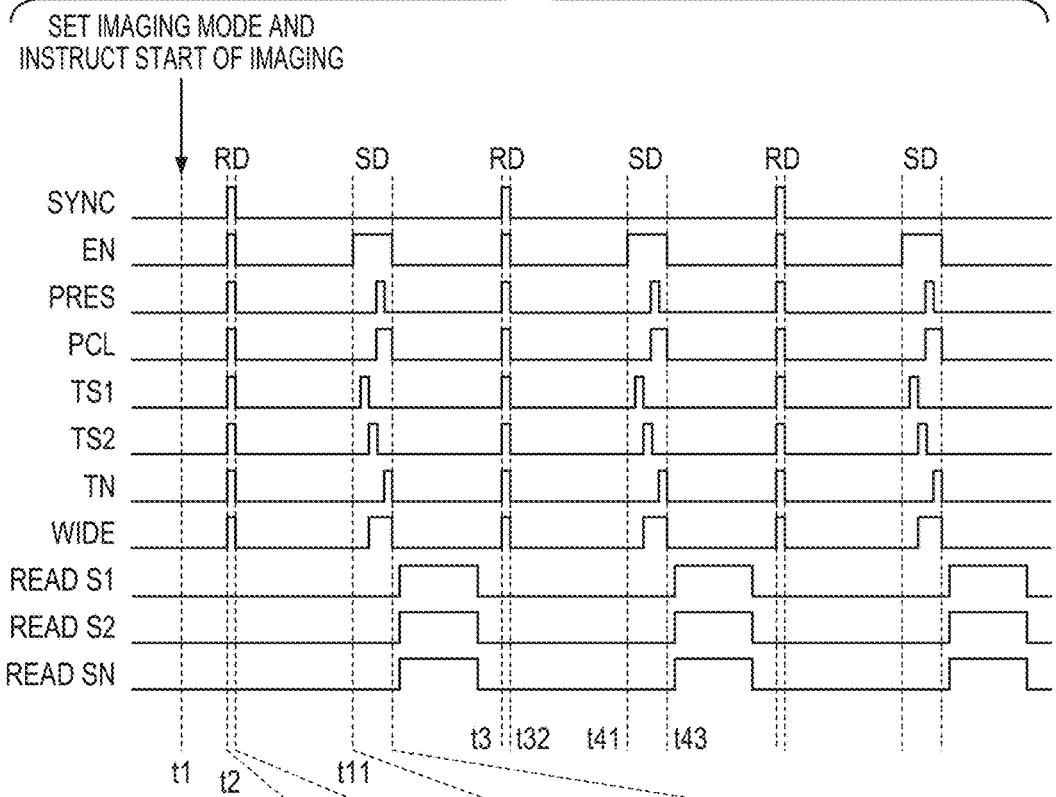
FIGS. 5A to 5C are timing charts exemplifying the operation of the radiation imaging apparatus according to the embodiment.
Figures 5B, 5C:
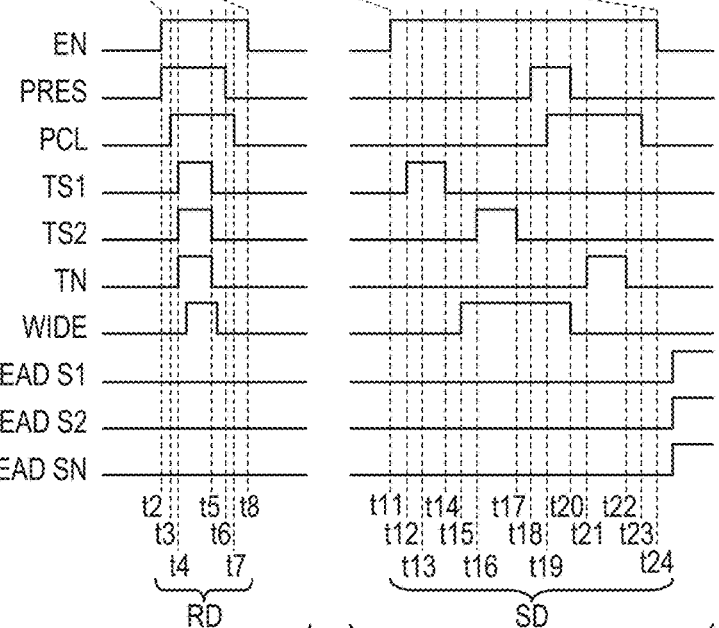

The operation mode of performing dynamic range expansion will be described below as one operation mode of the radiation imaging apparatus 100 with reference to FIGS. 5A to 5C, 6A, and 6B. FIG. 5A is a timing chart schematically showing an operation (moving image capturing operation) of capturing radiation images of a plurality of frames successively. FIG. 5B is a timing chart schematically showing reset driving RD in FIG. 5A. FIG. 5C is a timing chart schematically showing sampling driving SD in FIG. 5A. FIG. 6A is a timing chart schematically showing readout driving READ S1, READ S2, and READ SN in FIG. 5A. FIG. 6B is a timing chart obtained by partially enlarging a period in FIG. 6A.

At time t1, an operation mode (imaging mode) is set, and the start of imaging is instructed. Subsequently, at time t2, an operation for imaging is started. The operation for imaging is a repetition of cycles including the reset driving RD, the sampling driving SD, and the readout driving READ (READ S1, READ S2, and READ SN). The radiation image of one frame is captured in each cycle. The readout driving READ (READ S1, READ S2, and READ SN) is done after the reset driving RD followed by the sampling driving SD and before the next reset driving RD.

A reset operation and a clamp operation are performed in each reset driving RD. More specifically, as shown in FIG. 5B, the enable signal EN is driven at Hi level at time t2 to set the first control transistor M3 and the second control transistor M6 in the conductive state. This makes the first amplification transistor M4 and the second amplification transistor M7 ready for a source follower operation. At time t2, a signal PRES is also driven at Hi level to set the first reset transistor M2 in the conductive state. Consequently, the photodiode PD is connected to a reference voltage VRES, and reset of the photodiode PD is started. Also, a voltage corresponding to the gate voltage of the transistor M4 immediately after the start of reset is supplied to one terminal n1 of the clamp capacitor $C_{CL}$. At time t3, the signal PCL is driven at Hi level to set the second reset transistor M5 in the conductive state. Consequently, the clamp voltage VCL is supplied to the other terminal n2 of the clamp capacitor $C_{CL}$.

At time t4, the signals TS1, TS2, and TN are driven at Hi level to set the first transfer transistor M8, the second transfer transistor M11, and the third transfer transistor M14 in the conductive state. Consequently, all of the capacitors CS1, CS2, and CN are set in an initial state (a voltage of the output value of the amplification unit AP when the gate voltage of the second amplification transistor M7 is the reference voltage VCL). At time t4, the signal WIDE is also driven at Hi level to set the sensitivity switching transistor M1 in the conductive state. Consequently, the capacitor $C_{FD}'$ is connected to the reference voltage VRES, and the voltage of the capacitor $C_{FD}'$ is also reset. At time t5, the signals TS1, TS2, and TN are driven at Low level to set the first transfer transistor M8, the second transfer transistor M11, and the third transfer transistor M14 in the nonconductive state. Consequently, the voltages of the capacitors CS1, CS2, and CN are fixed. At time t5, the signal WIDE is also driven at Low level to set the sensitivity switching transistor M1 in the nonconductive state. Consequently, the capacitor $C_{FD}'$ is fixed to the reference voltage VRES. Then, at time t6, the signal PRES is driven at Low level to set the first reset transistor M2 in the nonconductive state. Consequently, the terminal n1 of the clamp capacitor $C_{CL}$ is set to a voltage corresponding to the gate voltage of the first amplification transistor M4 immediately after the end of reset. At time t7, the signal PCL is set at Low level to set the second reset transistor M5 in the nonconductive state. Consequently, the clamp capacitor $C_{CL}$ holds charges corresponding to the potential difference between the terminal n1 and the terminal n2, and the kTC noise of the conversion unit CP and the noise component such as the offset of the first amplification transistor. Consequently, the reset operation and the clamp operation are completed. Then, at time t8, the enable signal EN is driven at Low level to set the first control transistor M3 and the second control transistor M6 in the nonconductive state. Consequently, the first amplification transistor M4 and the second amplification transistor M7 are set in a non-operating state.

In the above manner, a series of operations in the reset driving RD are completed. That is, in the reset driving RD, the photodiode PD is reset, the clamp capacitor $C_{CL}$ holds the kTC noise of the conversion unit CP and the noise component arising from the offset of the first amplification transistor, and the capacitors CS1, CS2, and CN are initialized. Note that this reset driving RD is collectively performed for all the pixels P. That is, the respective control signals EN, PRES, PCL, TS1, TS2, TN, and WIDE are collectively supplied to all the pixels P at the same timing.

In the sampling driving SD in the operation mode of performing dynamic range expansion, each pixel P is driven with two sensitivities, and the capacitors CS1 and CS2 hold the signals obtained with two sensitivities. FIG. 5C shows a concrete operation. At time t11, the enable signal EN is driven at Hi level to set the first control transistor M3 and the second control transistor M6 in the conductive state, and make the first amplification transistor M4 and the second amplification transistor M7 be ready for the source follower operation. Note that at time t11, the signal WIDE is at Low level, and the pixels P are in a high-sensitivity mode corresponding to the first sensitivity. The gate voltage of the first amplification transistor M4 (that is, the voltage of the FD capacitor $C_{FD}$) changes in accordance with the amount of the charges generated and accumulated in the photodiode PD. A voltage corresponding to this changed gate voltage is supplied to one terminal n1 of the clamp capacitor $C_{CL}$, changing the potential of the terminal n1. The potential of the other terminal n2 of the clamp capacitor $C_{CL}$ changes in accordance with a change in the potential of the terminal n1. As described above, the clamp capacitor $C_{CL}$ holds a voltage corresponding to the kTC noise. Therefore, the amount of this potential change is output from the second amplification transistor M7 as a signal component.

At time t12, the signal TS1 is driven at Hi level to set the first transfer transistor M8 in the conductive state. That is, at time t12, sampling (transfer) of the output of the amplification unit AP in the high-sensitivity mode is started. More specifically, a voltage output from the amplification unit AP (a voltage corresponding to the gate voltage of the second amplification transistor M7) is transferred to the first holding capacitor CS1. Then, at time t13, an exposure permission signal (not shown) is driven at Low level (inhibited state) because sampling has started at time t12. Subsequently, at time t14, the signal TS1 is driven at Low level to set the first transfer transistor M8 in the nonconductive state. That is, at time t14, transfer of the voltage output from the amplification unit AP is completed, and the voltage held by the first holding capacitor CS1 is fixed. That is, at times t12 to t14, the first signal based on the charges of the conversion unit CP of the first sensitivity is sampled and held (holding) by the first holding capacitor CS1 of the first holding unit SH1.

At time t15, the signal WIDE is driven at Hi level to set the sensitivity switching transistor M1 in the conductive state. Consequently, the capacitor $C_{FD}'$ is electrically connected to the photodiode PD via the transistor M1, and the gate voltage of the transistor M4 becomes a voltage corresponding to a combined capacitor of the FD capacitor $C_{FD}$ and the capacitor $C_{FD}'$. Since the value of the composition capacitor is larger than the value of the FD capacitor $C_{FD}$, the gate voltage of the first amplification transistor M4 does not easily change. That is, the pixels P switch to the low-sensitivity mode corresponding to the second sensitivity. At time t16, the signal TS2 is driven at Hi level to set the second transfer transistor M11 in the conductive state. That is, at time t16, sampling (transfer) of the output of the amplification unit AP in the low-sensitivity mode is started. More specifically, the second holding capacitor CS2 becomes the voltage output from the amplification unit AP. Subsequently, at time t17, the signal TS2 is driven at Low level to set the second transfer transistor M11 in the nonconductive state. That is, at time t17, transfer of the voltage output from the amplification unit AP is completed, and the voltage held by the second holding capacitor CS2 is fixed. That is, at times t16 and t17, the second signal based on the charges of the conversion unit CP of the second sensitivity is sampled and held (holding) by the second holding capacitor CS2 of the second holding unit SH2.

Then, at time t18, the signal PRES is driven at Hi level to set the first reset transistor M2 in the conductive state. Consequently, the voltages of the FD capacitor $C_{FD}$ and the capacitor $C_{FD}'$ are reset to the reference voltage VRES, and the voltage of the terminal n1 is also reset to the same state as that at time t3. At time t19, the signal PCL is driven at Hi level to set the second reset transistor M5 in the conductive state. Consequently, the clamp voltage VCL is supplied to the other terminal n2 (a terminal on the side of the transistor M7) of the clamp capacitor $C_{CL}$. At time t20, the signals PRES and WIDE are driven at Low level to set the transistor M1 and the first reset transistor M2 in the nonconductive state. Consequently, the capacitor $C_{FD}'$ is fixed to a voltage immediately after the start of reset and in addition, the terminal n1 of the clamp capacitor $C_{CL}$ is set to a voltage corresponding to the gate voltage of the first amplification transistor M4 immediately after the start of reset. At time t21, the signal TN is driven at Hi level to set the third transfer transistor M14 in the conductive state. Consequently, a voltage output from the amplification unit AP when the gate voltage of the second amplification transistor M7 is the reference voltage VCL is transferred to the third holding capacitor CN.

At time t22, the signal TN is driven at Low level to set the third transfer transistor M14 in the nonconductive state. Consequently, the voltage of the third holding capacitor CN is fixed. That is, at times t21 and t22, the third holding capacitor CN holds an offset signal. This offset signal is based on a voltage corresponding to the noise component arising from the offset of the second amplification transistor M7 such as thermal noise, 1/f noise, a temperature difference, and process variations depending on the circuit arrangement of the amplification unit AP. Then, at time t23, the signal PCL is driven at Low level to set the second reset transistor M5 in the nonconductive state. At time t24, the enable signal EN is driven at Low level to set the first control transistor M3 and the second control transistor M6 in the nonconductive state. In the above manner, a series of operations in the sampling driving SD are completed. That is, in the sampling driving SD, the first holding capacitor CS1 holds the first signal obtained by the corresponding pixel P of the first sensitivity, the second holding capacitor CS2 holds the second signal obtained by the corresponding pixel P of the second sensitivity, and the third holding capacitor CN holds the offset signal of the amplification unit AP. Note that like the reset driving RD described above, the sampling driving SD can collectively be performed for all the pixels P to prevent the occurrence of a control timing shift in each imaging block 120. That is, the respective control signals EN, PRES, PCL, TS1, TS2, TN, and WIDE are collectively supplied to all the pixels P at the same timing.

As described above, each signal held by each holding unit of the corresponding one of the pixels P repeats, on the row basis, an operation of selecting the plurality of pixels P on the row basis and sequentially selecting the plurality of pixels P in the selected row for each column, thereby reading out the image signals from all the pixels P. This is indicated by the readout driving READ S1, READ S2, and READ SN of FIG. 5A, and will be described further with reference to FIGS. 6A and 6B. FIGS. 6A and 6B show control signals supplied to the control terminals VST, CLKV, $T_{RO1}$, $T_{RO2}$, HST, CLKH, and ADCLK shown in FIGS. 2 and 3.

In an example shown in FIGS. 6A and 6B, in a period of times t210 and t220 during which signals are read out from the pixels P on the first row, the radiation imaging apparatus 100 reads out the first signal from each pixel P in the first half period, and then reads out the second signal from each pixel P in the second half period. Note that when reading out a signal from each imaging block 120, Hi level is supplied to the terminal $E_{CS}$ of the imaging block 120, and the switch $SW_{CS}$ is in the conductive state.

At time t200, the terminal VST receives a start pulse. At time t210, upon receiving the clock signal CLKV, the vertical scanning circuit 403 outputs the control signals VSR to the output units OP1 to OP3 of the pixels P on the first row via the control line 405 on the first row. Consequently, the output switches SW9, SW12, and SW15 of the pixels P on the first row are set in the conductive state, selecting the pixels P on the first row. Subsequently, the signal $T_{RO1}$ is driven at Hi level over the time interval between times t211 and t215, and the signal $T_{RO2}$ is driven at Low level. This makes each pixel P on the first row ready to output the first signal.

At time t211, the terminal HST receives a start pulse. At time t212, the clock signal CLKH is received. The horizontal scanning circuit 404 sequentially shifts the selected column from the first column to the nth column every time the clock signal CLKH (transition to its active level) is received. The analog-to-digital converter 108 receives the clock signal ADCLK (transition to its active level) at time (for example, time t213) between transition to the active level of the clock signal CLKH and transition to the next active level. Then, the analog-to-digital converter 108 performs analog-to-digital conversion on the first signal from each pixel P on the selected column in response to transition to the active level of the clock signal ADCLK. Thereafter, for example, at time t214, the pixels P on the next column are selected, and the first signals from the pixels P are output and analog-to-digital-converted in the same manner. In this manner, the radiation imaging apparatus 100 sequentially performs a readout operation of the first signals from the first column to the nth column on a column basis. Subsequently, at time t215, the signal $T_{RO1}$ is driven at Low level, the signal $T_{RO2}$ is driven at Hi level, and a readout operation of the second signals from the first column to the nth column is sequentially performed on the column basis according to the same procedure as described above. In this case, the image data interface 111 can transmit the digital data from the control unit 109 to processing unit 101 for each row of the imaging unit 105 in the order in which they are read out by the readout units 106, obtaining an image signal for one frame. In the above operation, both an image signal based on the signal obtained with the first sensitivity and an image signal based on the signal obtained with the second sensitivity are read out. Then, an image signal which has undergone dynamic range expansion is obtained by combining the image signal based on the signal obtained with the first sensitivity and the image signal based on the signal obtained at the second sensitivity in correspondence with each pixel P.

Figure 15:
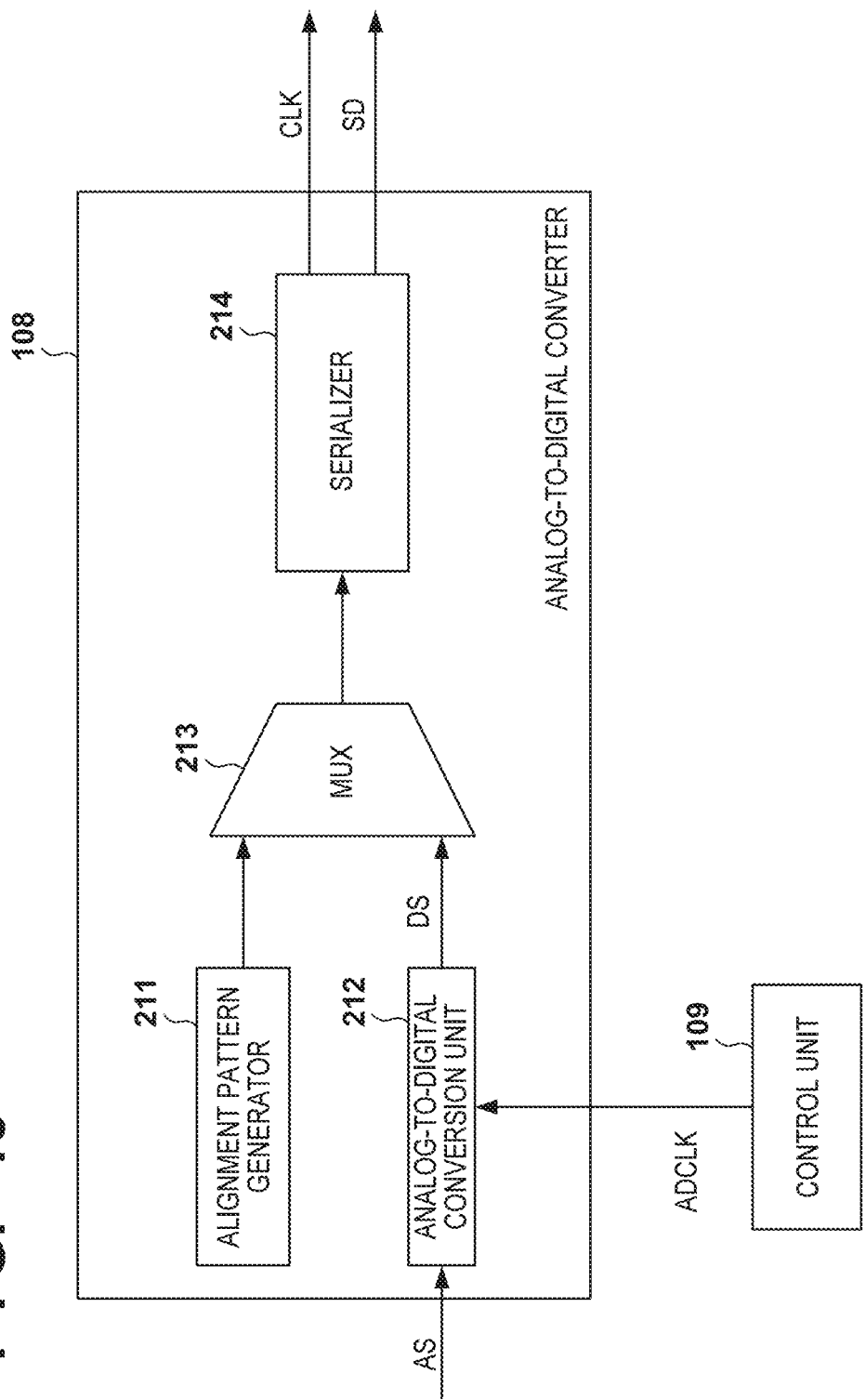
FIG. 15 is a block diagram showing the arrangement of an analog-to-digital converter of the readout circuit of the radiation imaging apparatus according to the embodiment.

FIG. 15 shows the arrangement of the analog-to-digital converter 108. The analog-to-digital converter 108 can include an analog-to-digital conversion unit 212, an alignment pattern generator 211, a selector 213, and a serializer 214. In accordance with a selection signal supplied from the control unit 109, the selector 213 selects one of a digital signal DS serving as a pixel signal supplied from the analog-to-digital conversion unit 212 and an alignment pattern supplied from the alignment pattern generator 211, and outputs it. The analog-to-digital conversion unit 212 performs, in accordance with the clock signal ADCLK, analog-to-digital conversion on the analog signal AS serving as a pixel signal supplied from the signal amplification unit 107 and outputs a conversion result as the digital signal DS made of data (parallel data) of a plurality of bits. The alignment pattern generator 211 generates the data (parallel data) of the plurality of bits serving as a preset alignment pattern (alignment marker). Accordingly, the selector 213 outputs the digital signal made of the data (parallel data) of the plurality of bits. The serializer 214 converts the digital signal DS made of the data of the plurality of bits output from the selector 213 into the serial data string of the plurality of bits serving as the serial data SD and outputs it. In accordance with the clock signal ADCLK, the analog-to-digital converter 108 also generates and outputs a serial clock CLK in synchronism with the serial data SD. The serializer 214 is not needed when the analog-to-digital conversion unit 212 and the alignment pattern generator 211 are configured to output serial data. The alignment pattern generator 211 can have a function of registering a designated alignment pattern.

Figure 16:
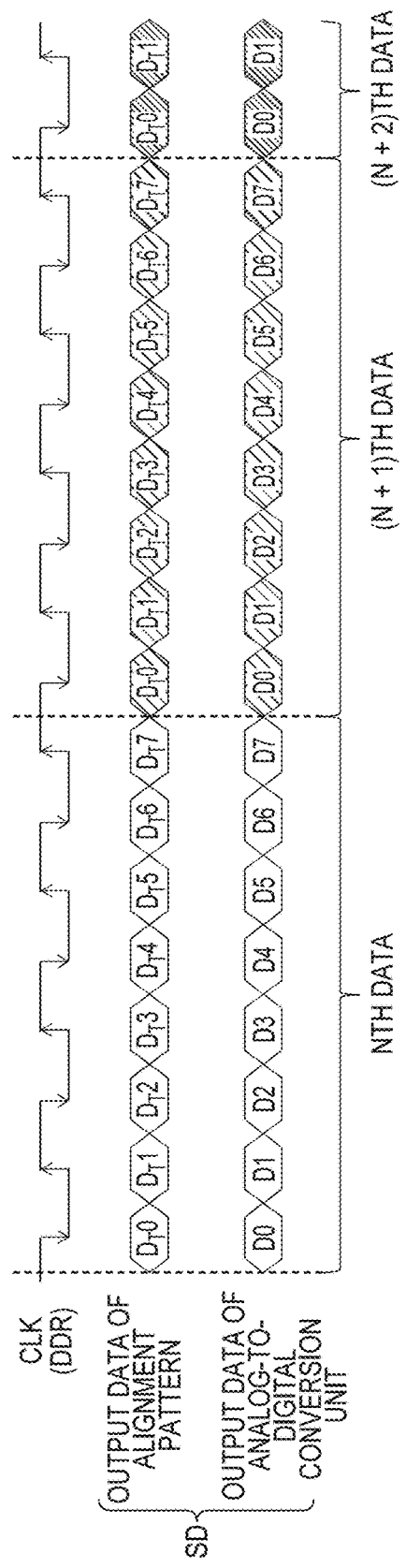
FIG. 16 is a view showing serial data output from the analog-to-digital converter.

FIG. 16 schematically shows the serial data SD output from the analog-to-digital converter 108. In reality, the serial data SD output from the analog-to-digital converter 108 is one of the analog signal AS supplied from the analog-to-digital conversion unit 212 ("output data of the analog-to-digital conversion unit in FIG. 16) and the alignment pattern supplied from the alignment pattern generator 211 ("output data of the alignment pattern" in FIG. 16). However, FIG. 16 shows both of them for the descriptive convenience. The serial clock CLK can be generated in a DDR format. The serial data string of the plurality of bits corresponding to one data (parallel data) can be formed, for example, with an LSB as a start bit. However, the serial data string may be formed with an MSB as a start bit. FIG. 16 shows the Nth data (parallel data), the (N+1)th data (parallel data), and the (N+2)th data (parallel data).

FIG. 16 describes the Nth data (parallel data), the (N+1)th data (parallel data), and the (N+2)th data (parallel data) identified with each other. For identification, however, alignment needs to be performed. Alignment is a process for identifying the serial data string corresponding to one data (parallel data) and made of the plurality of bits in serial data including the serial data string. A state in which alignment is not performed correctly is referred to as, for example, a state with a "bit shift".

Figure 14:
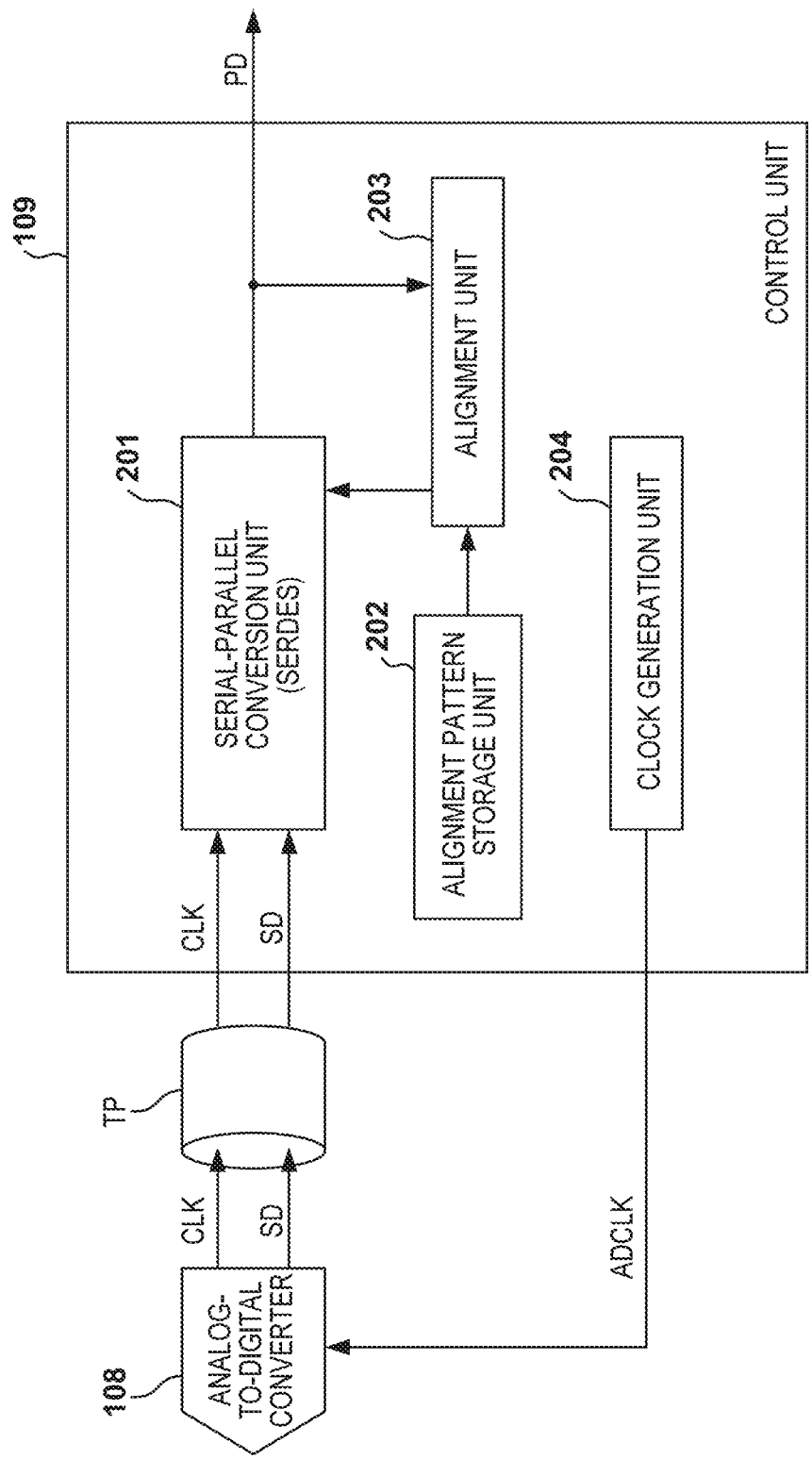
FIG. 14 is a block diagram showing the arrangement of a control unit of the radiation imaging apparatus according to the embodiment.

FIG. 14 shows the arrangement of the control unit 109. The control unit 109 can include a serial-parallel conversion unit 201, an alignment pattern storage unit 202, an alignment unit 203, and a clock generation unit 204. The serial data SD and the serial clock CLK output from the analog-to-digital converter 108 are transmitted to the serial-parallel conversion unit 201 of the control unit 109 via a transmission path TP. The transmission path TP can be, for example, a flexible cable. Note that the analog-to-digital converter 108 can include a transmission circuit which transmits the serial data SD and the serial clock CLK. The control unit 109 can also include a reception circuit which receives the serial data SD and the serial clock CLK. The transmission circuit and the reception circuit form a communication circuit. The communication circuit and the transmission path TP form a transmission unit. The clock generation unit 204 generates, for example, based on a basic clock generated by itself or a basic clock supplied outside, the clock ADCLK to be provided to the analog-to-digital converter 108.

The serial-parallel conversion unit 201 receives the serial data SD in accordance with the serial clock CLK and converts the serial data SD into parallel data PD. The alignment pattern storage unit 202 stores an alignment pattern used for alignment. The alignment unit 203 performs alignment by comparing the alignment pattern in the serial data SD transmitted from the analog-to-digital converter 108 with the alignment pattern stored in the alignment pattern storage unit 202. This alignment can be a process of identifying the start bit in the serial data string. The start bit in the serial data string can be identified when, for example, the serial data string (alignment pattern) in the serial data SD transmitted from the analog-to-digital converter 108 and the alignment pattern stored in the alignment pattern storage unit 202 match.

As a more concrete example, a case will be considered in which individual parallel data is made of n bits. In this case, serial data corresponding to the individual parallel data is made of an n-bit serial data string. The serial-parallel conversion unit 201 can be configured to cause a counter which repeats a count operation of counting from 0 to (n–1) to operate in accordance with the serial clock CLK and receive the serial data as the start bit when the count value of the counter is 0. The alignment unit 203 can reset the counter in accordance with the match between the serial data string (alignment pattern) in the serial data SD transmitted from the analog-to-digital converter 108 and the alignment pattern stored in the alignment pattern storage unit 202. This reset is alignment. Alignment can also be performed by resetting the serial-parallel conversion unit 201 in accordance with the match between the serial data string (alignment pattern) in the serial data SD and the alignment pattern stored in the alignment pattern storage unit 202.

Figure 19:
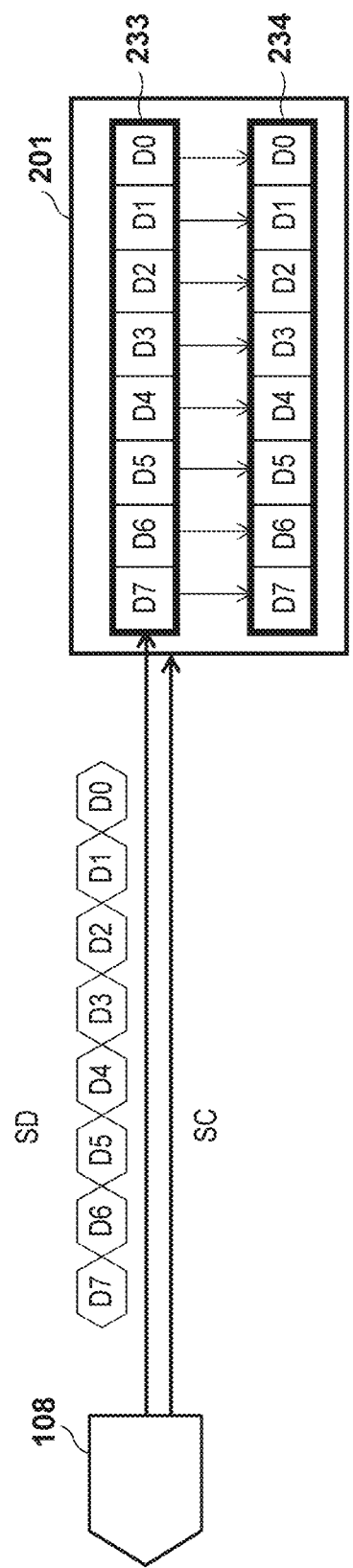
FIG. 19 is a view showing an example of serial-parallel conversion in a serial-parallel conversion unit of the control unit of the radiation imaging apparatus according to the embodiment.

FIG. 19 schematically shows an example of serial-parallel conversion in the serial-parallel conversion unit 201. In this example, the serial data SD corresponding to one parallel data is made of an 8-bit serial data string. The serial-parallel conversion unit 201 can include a shift register 233 and an output register 234. The 8-bit serial data string of the serial data SD is received by the shift register 233 in the serial-parallel conversion unit 201 in accordance with eight edges of a serial clock SC. The counter can count eight edges. Once the 8-bit serial data string is received by the shift register 233, parallel transfer of the 8-bit serial data string to the output register 234 as parallel data is performed at once, and then the parallel data is output from the output register 234.

As shown in FIG. 16, the digital signal DS from the analog-to-digital conversion unit 212 ("the output data of the analog-to-digital conversion unit") and the alignment pattern from the alignment pattern generator 211 ("the output data of the alignment pattern") are output at the same timing. Therefore, by performing alignment using the alignment pattern, it is possible, afterward, to convert the serial data SD which is generated from the digital signal DS output from the analog-to-digital conversion unit 212 into the parallel data PD correctly.

In an example shown in FIG. 14, the serial-parallel conversion unit 201, the alignment pattern storage unit 202, and the alignment unit 203 exist in the control unit 109. However, all or some of the serial-parallel conversion unit 201, the alignment pattern storage unit 202, and the alignment unit 203 may exist outside the control unit 109.

Figure 7:
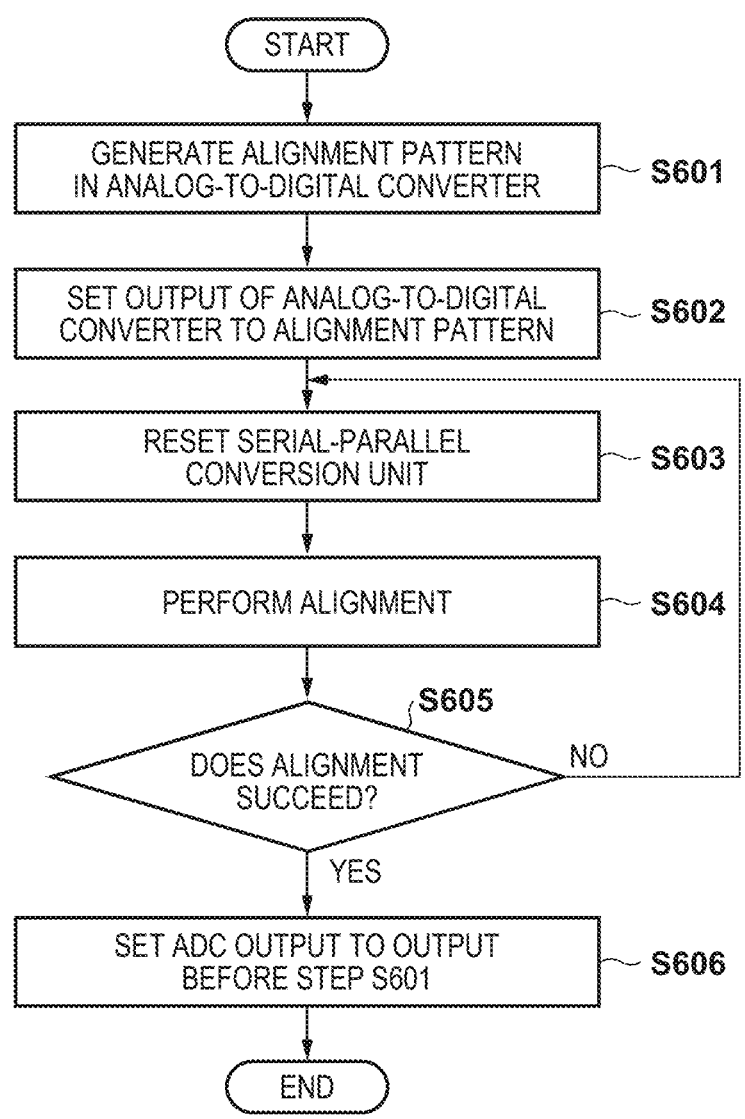
FIG. 7 is a flowchart showing an alignment method in the radiation imaging apparatus according to the embodiment.
Figure 17:
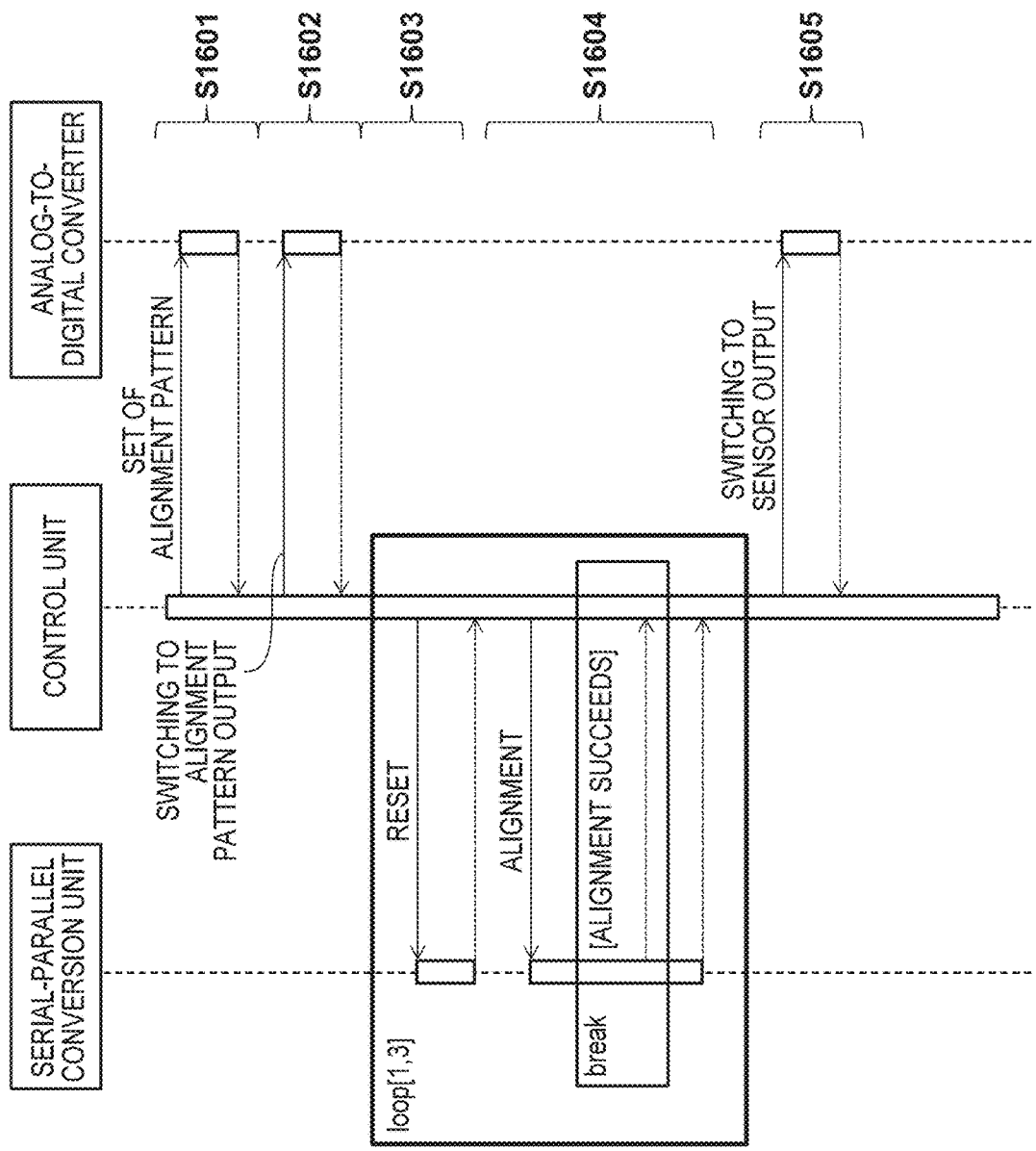
FIG. 17 is a sequence chart showing the alignment method in the radiation imaging apparatus according to the embodiment.
Figure 18:
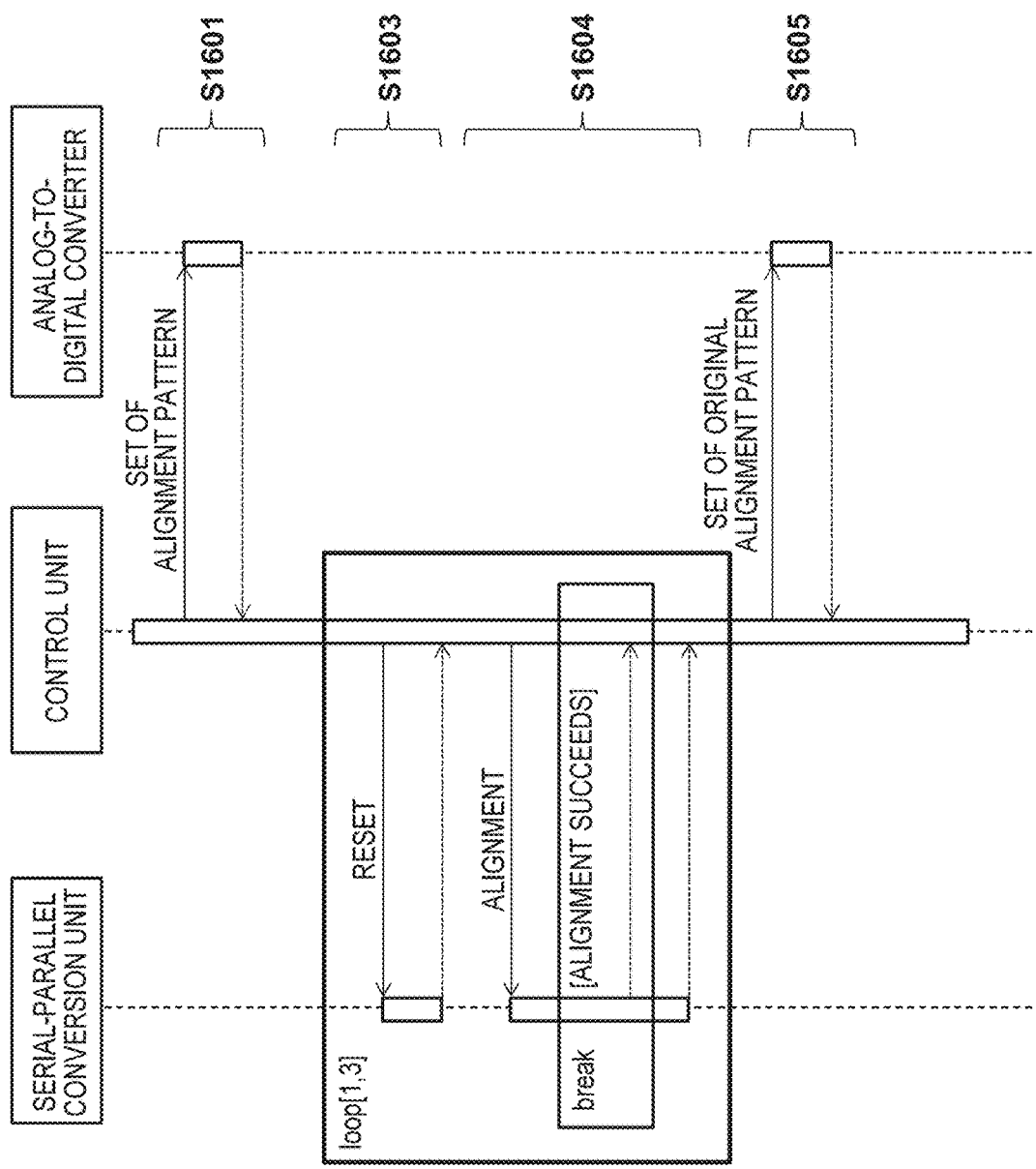
FIG. 18 is a sequence chart showing the alignment method in the radiation imaging apparatus according to the embodiment.

An alignment method by the alignment unit 203 (a control method of the radiation imaging apparatus 100) will be described with reference to FIGS. 7, 17, and 18. In steps S601 and S1601, the alignment unit 203 sets alignment patterns in the alignment pattern generator 211 of the analog-to-digital converter 108 and the alignment pattern storage unit 202 of the control unit 109. The alignment pattern generator 211 generates the set alignment pattern. The alignment pattern can be, for example, 0xF0. "0x" means hexadecimal notation.

In steps S602 and S1602, the alignment unit 203 controls the selector 213 of the analog-to-digital converter 108 to select and output the alignment pattern supplied from the alignment pattern generator 211.

In steps S603 and S1603, the alignment unit 203 resets the serial-parallel conversion unit 201. Considering a case in which, for example, the bit shift has occurred owing to external noise or the like, it is preferable that the serial-parallel conversion unit 201 is reset in an initial state before performing alignment. Subsequently, in steps S604 and S1604, the alignment unit 203 performs alignment of the serial-parallel conversion unit 201. As described above, the alignment unit 203 performs alignment by comparing the alignment pattern in the serial data SD transmitted from the analog-to-digital converter 108 with the alignment pattern stored in the alignment pattern storage unit 202. This alignment can be the process of identifying the start bit in the serial data string.

Assuming that comparison of two alignment patterns is completed in one clock (one cycle of the CLK), it is possible to identify the start bit of the serial data string and complete alignment within eight cycles at most as long as two alignment patterns match. A case in which the start bit can be identified within eight cycles is success; otherwise, failure. In step S605, the alignment unit 203 judges whether alignment succeeds. If alignment fails, the process repeats steps S602 to S605. If alignment succeeds, the process advances to step S606. In steps S606 and S1605, the alignment unit 203 returns the output of the analog-to-digital converter 108 to a state before step S601. If the output of the analog-to-digital converter 108 is the output of a signal from the corresponding imaging block 120, the alignment unit 203 switches the selector 213 of the analog-to-digital converter 108 so as to output the signal from the imaging block 120. Note that the output of the analog-to-digital converter 108 (the state of the selector 213) before step S601 is saved before performing step S601.

For example, if the alignment pattern from the alignment pattern generator 211 is output from the analog-to-digital converter 108 for a test before step S601, such a state is returned in steps S606 and S1605.

If alignment continuously fails over a preset number of times, the process may advance to steps S606 and S1605, or moving image capturing may be stopped even if alignment does not succeed. In an example shown in FIG. 17, if alignment fails three times, a process for alignment is terminated. For example, a setting error in the analog-to-digital converter 108, an incorrect alignment pattern stored in the alignment pattern storage unit 202, susceptibility to external noise during alignment, or the like is considered as a cause of failing alignment.

Figure 8:
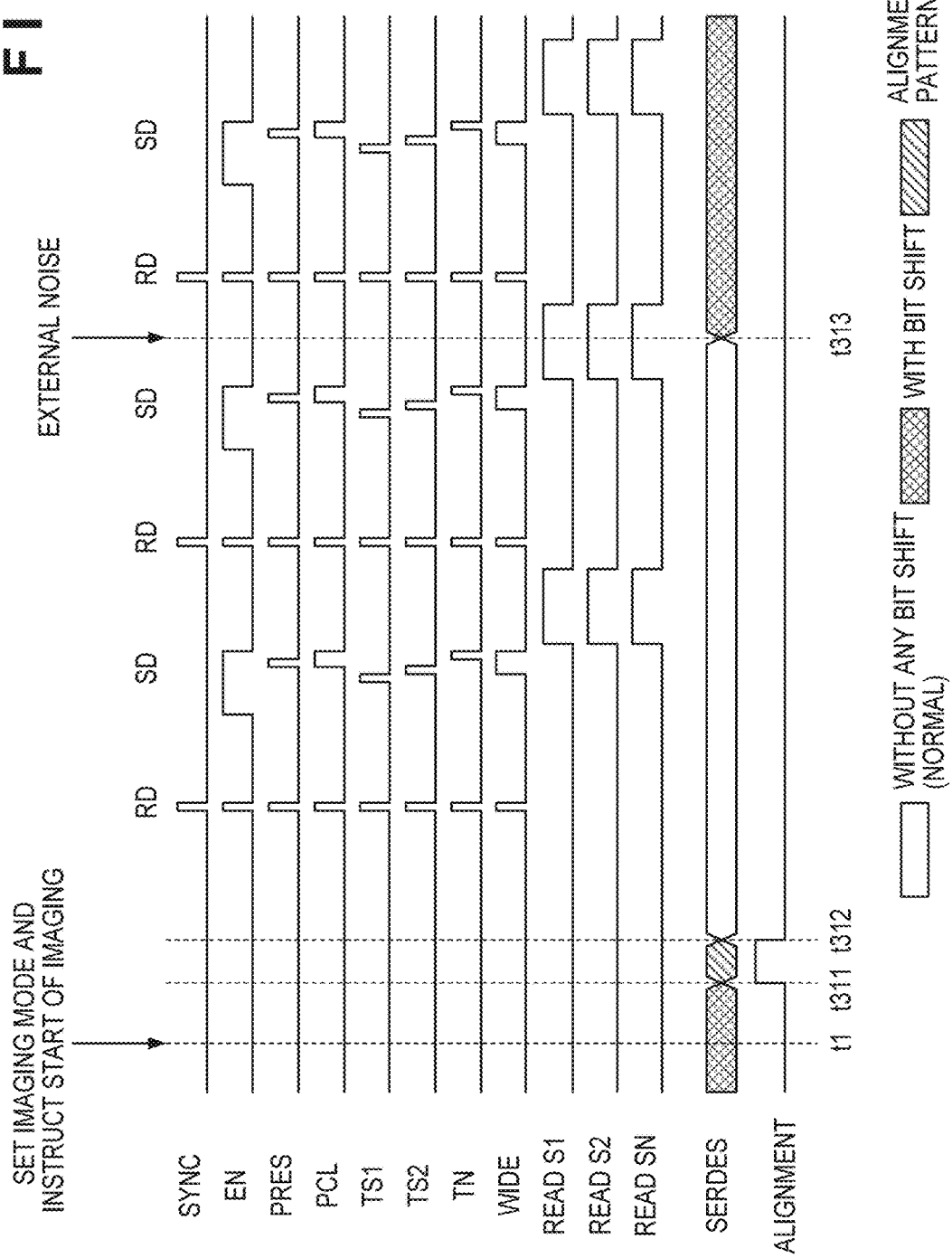
FIG. 8 is a timing chart showing a comparative example.

FIG. 8 shows, as a comparative example, an example in which alignment is performed just once before imaging starts. Basic driving is the same as in FIG. 5. After an imaging mode is set, and the start of imaging is instructed at time t1, alignment is performed in a period between time t311 and time t312. In FIG. 8, "SERDES" indicates the output of the serial-parallel conversion unit 201 (ditto for other drawings). A crosshatched portion indicates the state with the bit shift or a state in which the output value of the serial-parallel conversion unit 201 cannot be ensured because alignment is not performed. A hatched portion indicates a state in which the alignment pattern is output, that is, a state in which an alignment process is in progress. A white portion indicates a state in which alignment is completed and there is no bit shift.

In the example of FIG. 8, a period up to time t311 indicates the state in which the output value cannot be ensured, the period between the time t311 and time t312 indicates the state in which alignment is in progress, and a period between time t312 and time t313 indicates the state without any bit shift. At time t313, the bit shift occurs in the serial-parallel conversion unit 201 owing to external noise such as static electricity. In the example of FIG. 8, alignment is performed only once before imaging starts, and thus it is impossible to return from the state with the bit shift even after the external noise such as the static electricity is removed.

Figure 9:
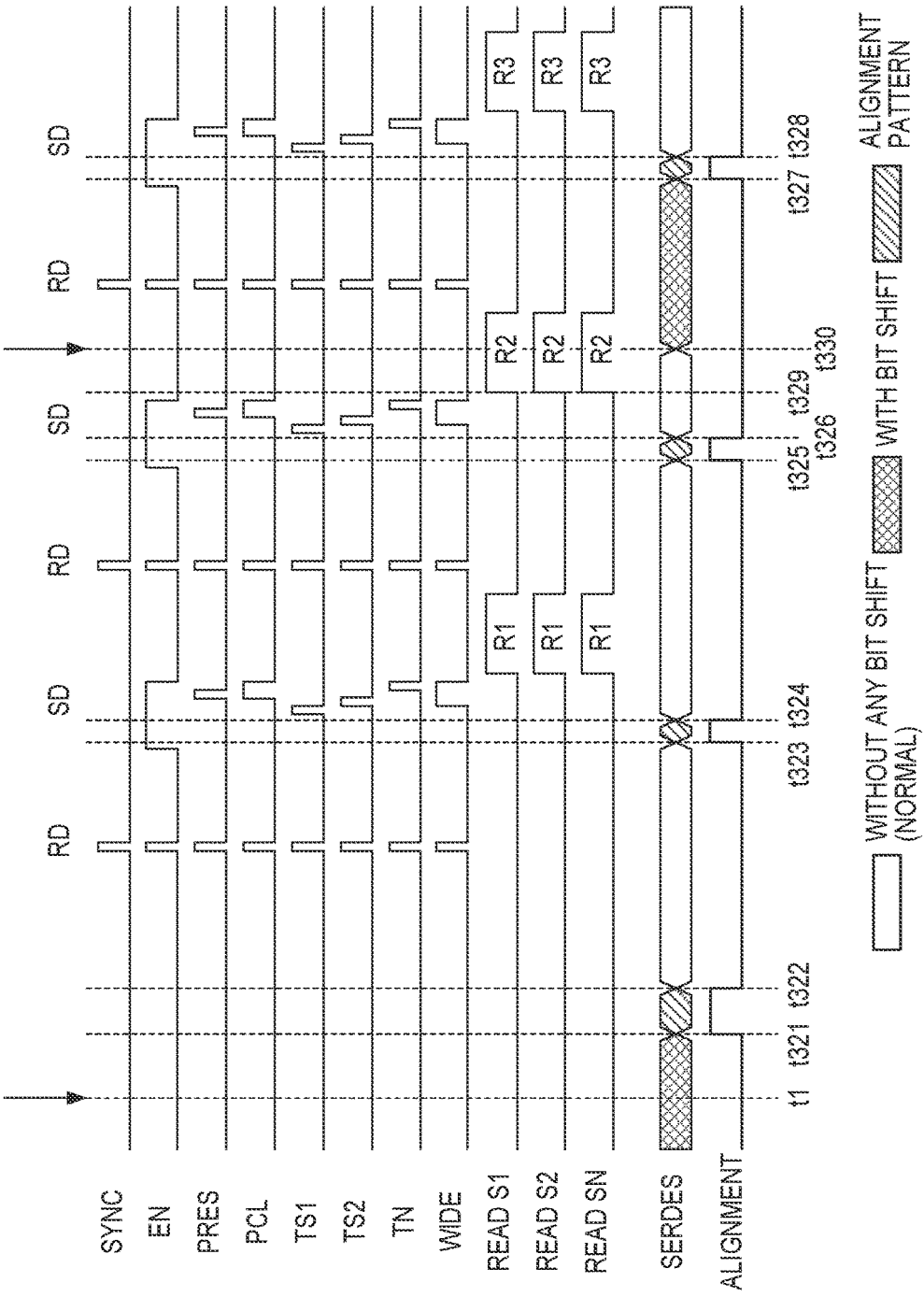
FIG. 9 is a timing chart showing the first operation example of the radiation imaging apparatus according to the embodiment.

FIG. 9 shows the first operation example of the radiation imaging apparatus 100. In moving image capturing of capturing the radiation images of the plurality of frames successively, a cycle including the reset driving RD and the sampling driving SD is repeated a plurality of times. Following each sampling driving SD, the readout driving READ is performed. Note that a period during which the reset driving RD is performed is defined as a reset driving period, a period during which the sampling driving SD is performed is defined as a sampling driving period, and a period during which the readout driving READ is performed is defined as a readout driving period. As described with reference to FIGS. 6A and 6B, the readout driving period includes a period during which the analog-to-digital converter 108 performs analog-to-digital conversion. The period during which the analog-to-digital converter 108 performs analog-to-digital conversion is defined as an analog-to-digital conversion period. A plurality of reset driving periods correspond to the plurality of frames. A plurality of sampling driving periods correspond to the plurality of frames. A plurality of readout driving periods correspond to the plurality of frames. A plurality of analog-to-digital conversion periods correspond to the plurality of frames. In each of the plurality of analog-to-digital conversion periods corresponding to the plurality of frames, the analog-to-digital converter 108 converts individual analog signals from the imaging unit 105 into digital signals and outputs the converted individual digital signals as the serial data string of the plurality of bits.

After the imaging mode is set, and the start of imaging is instructed at time t1, the alignment unit 203 performs alignment in a period between time t321 and time t322. Note that the period between time t321 and time t322 is a period before the first readout driving period out of the plurality of readout driving periods. In other words, the period between time t321 and time t322 is a period before the plurality of analog-to-digital conversion periods.

In the first operation example, the alignment unit 203 further performs alignment also in periods between t323 and t324, t325 and t326, and t327 and t328 each serving as the sampling driving period. The readout driving READ is not performed in the sampling driving periods, and thus reset (alignment) of the serial-parallel conversion unit 201 or an operation of outputting the alignment pattern from the analog-to-digital converter 108 does not influence the image data output from the radiation imaging apparatus 100. Note that a sampling period is between the read driving period and the next readout driving period. In other words, the sampling period is between the analog-to-digital conversion period and the next analog-to-digital conversion period. Hence, in the first operation example, alignment is performed in a period between each of the plurality of analog-to-digital conversion periods and the next analog-to-digital conversion period, in addition to being performed before the first analog-to-digital conversion period out of the plurality of analog-to-digital conversion periods.

Assume that a bit shift occurs in the serial-parallel conversion unit 201 owing to external noise such as static electricity at time t330 in a second readout driving period (R2) started from time t329. In the first operation example, alignment is performed between t327 and t328, and thus a normal state without any bit shift is obtained from t328. That is, even if an image abnormality is caused by a bit shift in a certain frame, an image of the next frame can return to a normal image. In the operation example of FIG. 9, an abnormality is caused, midway through readout, in an image read out in the second readout driving period (R2) by the bit shift by the external noise such as the static electricity, but an image read out in a third readout period (R3) returns to a normal image. That is, in the operation example of FIG. 9, even if a bit shift is caused in the serial-parallel conversion unit 201 of a certain frame by external noise such as static electricity, the bit shift can be corrected before the readout driving READ of the next frame. It is therefore possible to minimize a degree to which external noise influences an image.

Figure 10:
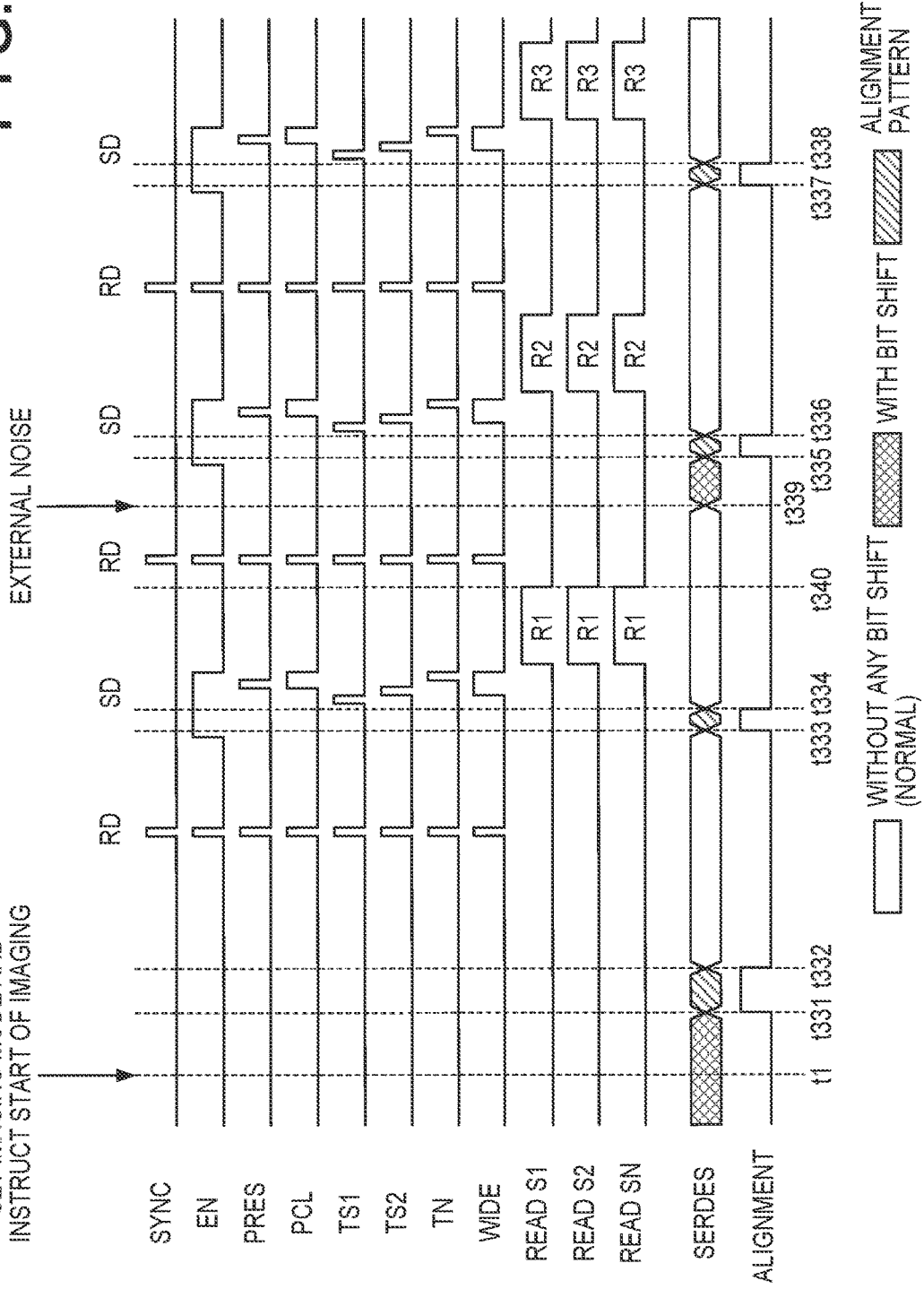
FIG. 10 is a timing chart showing the first operation example of the radiation imaging apparatus according to the embodiment.

FIG. 10 shows a case in which, in the first operation example, the bit shift by the external noise occurs at a timing different from that in the example shown in FIG. 9. In an example shown in FIG. 10, a bit shift by the external noise such as the static electricity occurs at time t339 between a first readout driving period (R1) and the second readout driving period (R2). Even if the bit shift occurs at time t339, the bit shift is corrected by alignment performed between t335 and t336. Thus, the image read out in the second readout driving period (R2) is normal. That is, the image is not influenced as long as no bit shift occurs between t334 and t340, that is, from the end of alignment to the end of the subsequent readout driving period. For example, when moving image capturing is performed at 30 fps, a period between t334 and t340 is several msec relative to a readout cycle of 33 msec, and thus a probability of the bit shift by the external noise or the like is decreased, making it possible to well suppress the influence on the image by the external noise or the like.

In the first operation example shown in FIGS. 9 and 10, alignment is performed before TS1 or the like is asserted out of a sampling driving period (SD). However, this is merely an example. As described above, the sampling driving period (SD) does not involve readout of the image signal from the analog-to-digital converter 108, and thus alignment can be performed anytime in the sampling driving period. However, alignment needs to be completed before the readout driving period starts.

Figure 11:
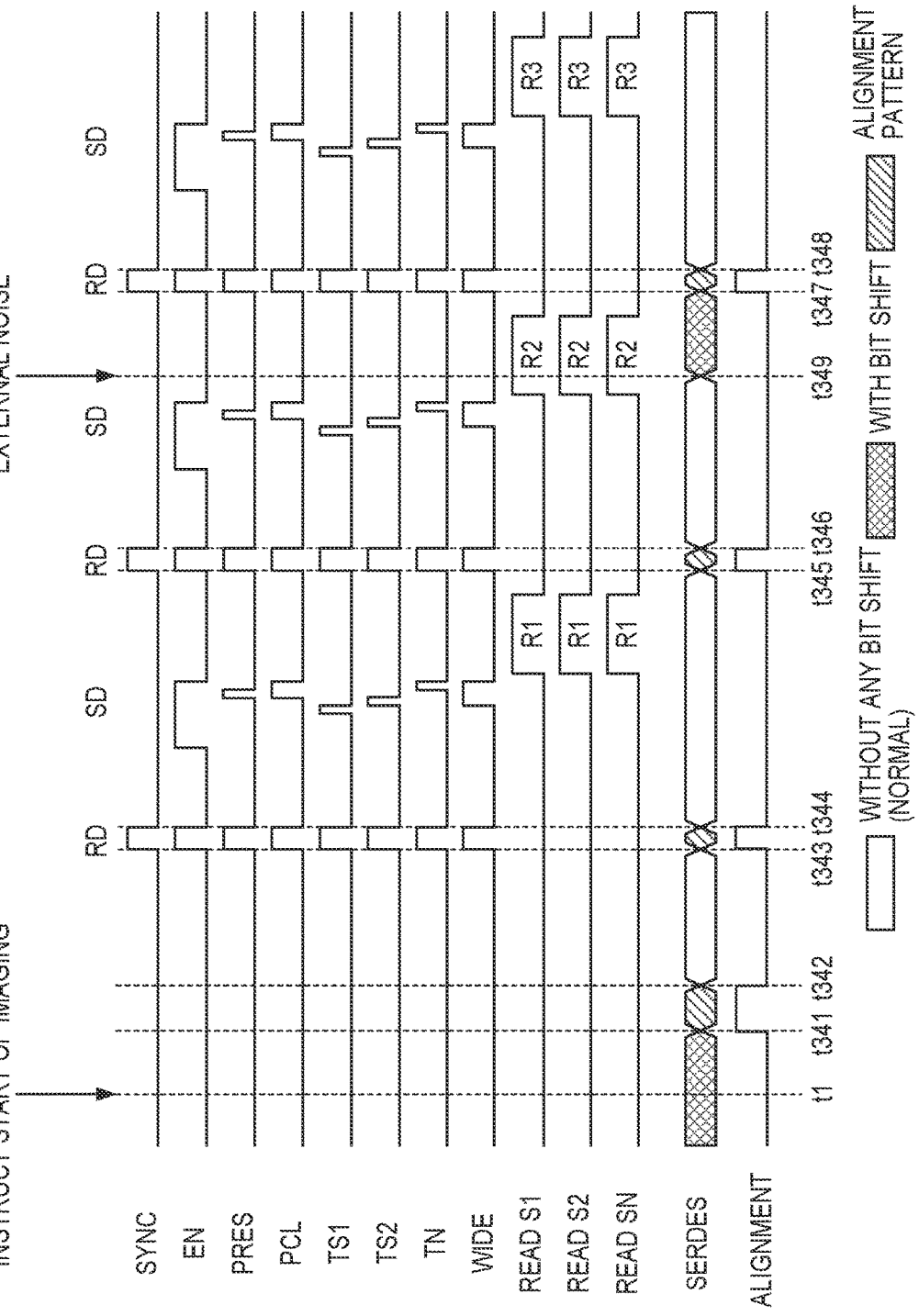
FIG. 11 is a timing chart showing the second operation example of the radiation imaging apparatus according to the embodiment.

FIG. 11 shows the second operation example of the radiation imaging apparatus 100. The second operation example is different from the first operation example in timing of performing alignment. In the second operation example, after the imaging mode is set, and the start of imaging is instructed at time t1, the alignment unit 203 performs alignment in a period between t341 and t342, that is, a period before the first reset driving period (RD). However, this alignment can be omitted.

In the second operation example, the alignment unit 203 further performs alignment also between t343 and t344, t345 and t346, and t347 and t348 each serving as the reset driving period (RD). The readout driving READ is not performed in the reset driving periods (RD), and thus reset (alignment) of the serial-parallel conversion unit 201 or the operation of outputting the alignment pattern from the analog-to-digital converter 108 does not influence the image data output from the radiation imaging apparatus 100.

Also in the second operation example, alignment is performed in the period between each of the plurality of analog-to-digital conversion periods and the next analog-to-digital conversion period, in addition to being performed before the first analog-to-digital conversion period out of the plurality of analog-to-digital conversion periods.

Assume that a bit shift occurs in the serial-parallel conversion unit 201 owing to external noise such as static electricity at time t349. In the second operation example, alignment is performed in a period between t347 and t348 serving as the reset driving period, and thus a normal state without any bit shift is obtained from t348. That is, even if an image abnormality is caused by a bit shift in a certain frame, an image of the next frame can return to a normal image. In the example of FIG. 11, an abnormality is caused in an image read out in the second readout driving period (R2) by the bit shift by the external noise such as the static electricity, but an image read out in the third readout period (R3) returns to a normal image.

Figure 12:
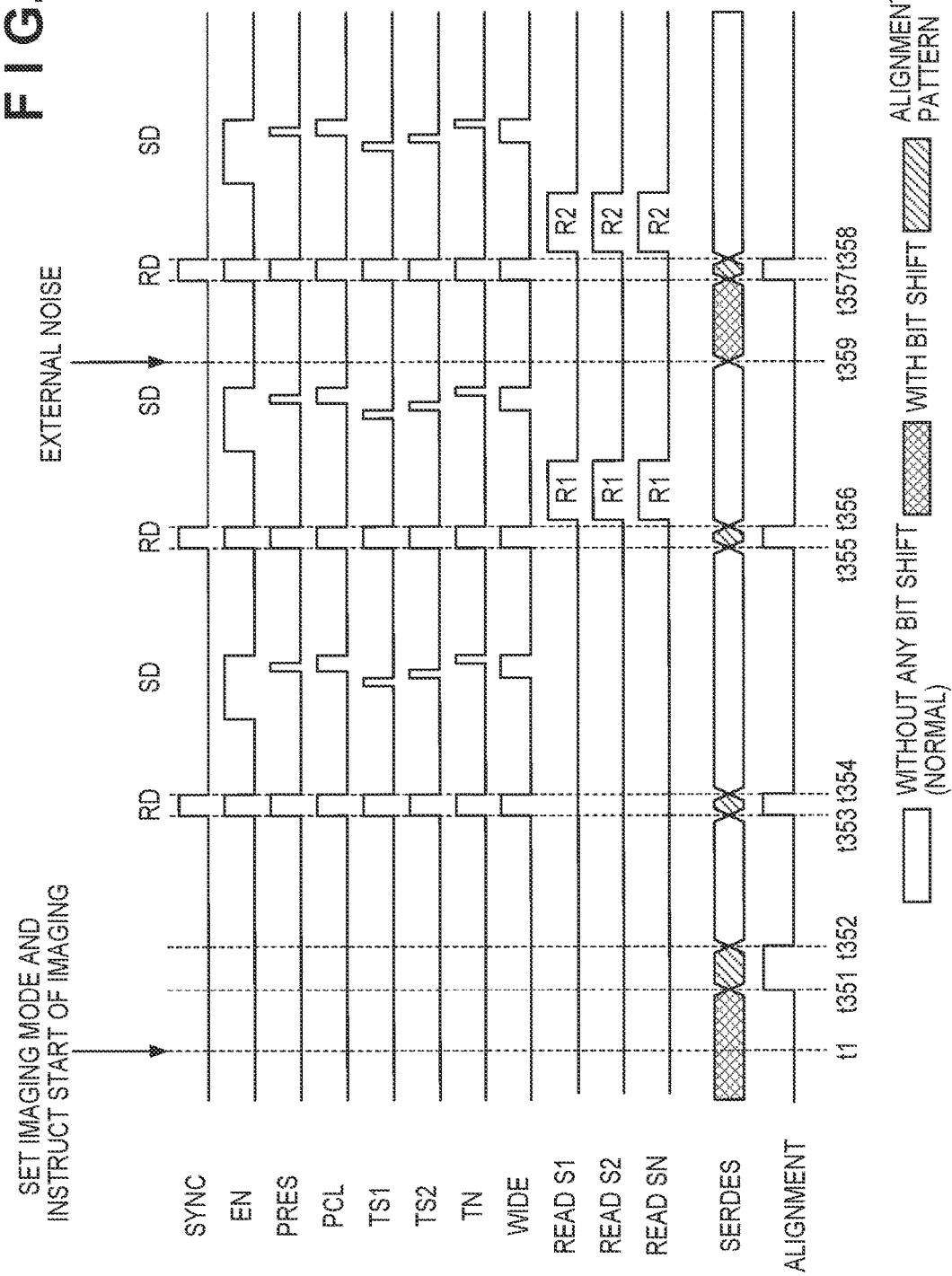
FIG. 12 is a timing chart showing a modification of the second operation example of the radiation imaging apparatus according to the embodiment.

FIG. 12 shows an operation of a modification in the second operation example. In the modification, the readout driving periods (R1 and R2) follow the reset driving period (RD). The reset driving periods (RD) of t355 and t356, and t357 and t358 are arranged immediately before the corresponding readout driving periods (R1 and R2). Therefore, even if a bit shift by external noise such as static electricity occurs at time t359, the bit shift can be corrected before the readout driving period (R2) of the next frame starts, making it possible to minimize the influence on the image.

Alignment can be performed in a period during which the readout driving READ is not performed. It is therefore possible to obtain a higher effect if a timing at which the readout driving READ is performed is known based on the imaging mode, and alignment is performed at a timing according to it.

In the first operation example and the second operation example, alignment is performed once per frame. However, this is merely an example. Alignment may be performed a plurality of times per frame or once in several frames. Alternatively, alignment may be performed once in a predetermined time.

That is, the alignment unit 203 can be configured to perform alignment in a period between, out of the plurality of readout driving periods, at least one readout driving period and another readout driving period, in addition to performing alignment before the first readout driving period out of the plurality of readout driving periods. In other words, the alignment unit 203 can be configured to perform alignment in at least a period between, out of the plurality of analog-to-digital conversion periods, one analog-to-digital conversion period and another analog-to-digital conversion period, in addition to performing alignment before the first analog-to-digital conversion period out of the plurality of analog-to-digital conversion periods.

From the viewpoint of reducing the influence of the bit shift, the alignment unit 203 preferably performs alignment at least once in a period during which a signal of one frame is read out from the imaging unit 105 via the analog-to-digital converter 108 and the serial-parallel conversion unit 201. Furthermore, from the viewpoint of further reducing the influence of the bit shift, the alignment unit 203 preferably performs alignment at least twice in the period during which the signal of one frame is read out from the imaging unit 105 via the analog-to-digital converter 108 and the serial-parallel conversion unit 201.

Figure 13:
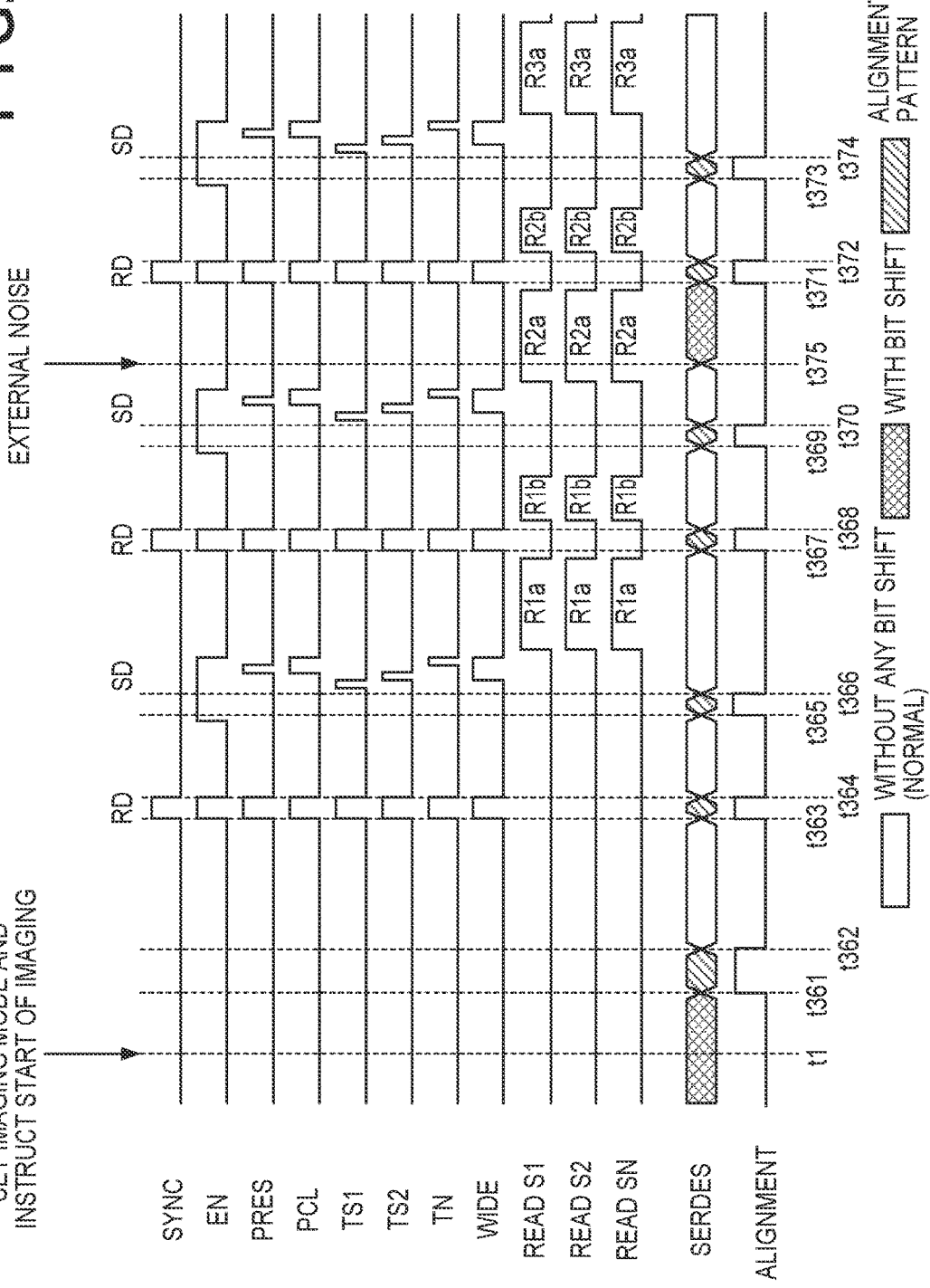
FIG. 13 is a timing chart showing the third operation example of the radiation imaging apparatus according to the embodiment.

FIG. 13 shows the third operation example of the radiation imaging apparatus 100. In the third operation example, the alignment unit 203 performs alignment twice per frame. After the imaging mode is set, and the start of imaging is instructed at time t1, the alignment unit 203 performs alignment in a period between time t361 and time t362. The alignment unit 203 also performs alignment in respective periods between t365 and t366, t369 and t370, and t373 and t374 each serving as the sampling driving period (SD). The alignment unit 203 further performs alignment in respective periods between t363 and t364, t367 and t368, and t371 and t372 each serving as the reset driving period (RD). Since the readout driving READ is not performed in the reset driving periods (RD) and the sampling driving periods (SD), reset of the serial-parallel conversion unit 201 or an operation of outputting a test pattern from the analog-to-digital conversion unit does not influence the image data.

In the example shown in FIG. 13, a synchronization signal SYNC of the next frame is received while performing the readout driving READ on a certain frame, interrupting the readout driving READ and starting the reset driving RD. Then, the interrupted readout driving READ is resumed after the end of the reset driving RD. The Nth readout driving READ before interruption is referred to as RN-a, and the Nth readout driving READ which is resumed after the end of the reset driving RD is referred to as RN-b.

Assume that a bit shift occurs in the serial-parallel conversion unit 201 owing to external noise such as static electricity at time t375. In the third operation example, alignment is performed between t371 and t372, and thus a normal state without any bit shift is obtained from t372. In the third operation example shown in FIG. 13, an abnormality is caused by the bit shift by the external noise such as the static electricity in an image read out in readout driving R2a. However, an image read out in readout driving R2b is returned to a normal image.

As described above, in the imaging mode in which the readout driving READ is performed across the reset driving RD operations, alignment can be performed in the periods of the reset driving RD and the periods of the sampling driving SD. This makes it possible to perform alignment twice per frame. According to the third operation, even if the bit shift by the external noise such as the static electricity occurs at time t375, it is possible to correct the bit shift before the next readout driving READ starts and to minimize the influence on the image.

Each of the above operations has been described regarding the operation mode of performing dynamic range expansion. However, the present invention is also applicable to an operation mode of not performing dynamic range expansion.

An example in which the radiation imaging system SYS is applied to a C-arm type radiation fluoroscopic examination system will be described with reference to FIG. 20. The radiation imaging apparatus 100 and the radiation source 104 are fixed to both ends of a C-arm cr. In this system, radiation imaging (3D imaging) is performed while changing a radiation irradiation angle with respect to a subject to be examined by rotating the arm cr. Image data obtained by the radiation imaging apparatus 100 is output to the processing unit 101 via, for example, a cable. The processing unit 101 forms a three-dimensional radiation image based on the image data and displays it on the display unit 102.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-010870, filed Jan. 22, 2016, which is hereby incorporated by reference herein in its entirety.

What is claimed is:

1. A radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the apparatus comprising:

an imaging unit having a plurality of sensors configured to detect radiation, and configured to output an analog signal from each of the plurality of sensors;

an analog-to-digital converter configured to, in each of a plurality of analog-to-digital conversion periods corresponding to the plurality of frames, convert the individual analog signals from the imaging unit into individual digital signals and output the individual digital signals as a serial data string of a plurality of bits;

a serial-parallel conversion unit configured to convert, into parallel data, the serial data string of the plurality of bits transmitted from the analog-to-digital converter via a transmission path; and an alignment unit configured to perform alignment for the serial-parallel conversion unit to identify the serial data string of the plurality of bits such that the processor correctly receives the signals for the radiation images of the plurality of frames from the apparatus, wherein the alignment unit performs the alignment in at least a period between, out of the plurality of analog-to-digital conversion periods.

2. The apparatus according to claim 1, further comprising a holding unit configured to sample and hold signals from the plurality of sensors, wherein the alignment unit performs the alignment in a period during which the holding unit performs sampling, in addition to performing the alignment before a first analog-to-digital conversion period out of the plurality of analog-to-digital conversion periods.

3. The apparatus according to claim 1, further comprising a reset unit configured to reset the plurality of sensors, wherein the alignment unit performs the alignment in a period during which the reset unit resets the plurality of sensors, in addition to performing the alignment before a first analog-to-digital conversion period out of the plurality of analog-to-digital conversion periods.

4. The apparatus according to claim 1, further comprising a holding unit configured to sample and hold signals from the plurality of sensors, and
a reset unit configured to reset the plurality of sensors, wherein
the alignment unit performs the alignment in a period during which the holding unit performs sampling and a period during which the reset unit resets the plurality of sensors, in addition to performing the alignment before a first analog-to-digital conversion period out of the plurality of analog-to-digital conversion periods.

5. The apparatus according to claim 1, wherein the alignment unit performs the alignment in a period between each of the plurality of analog-to-digital conversion periods and the next analog-to-digital conversion period, in addition to performing the alignment before a first analog-to-digital conversion period out of the plurality of analog-to-digital conversion periods.

6. The apparatus according to claim 1, wherein the alignment unit performs the alignment at least once in a period during which a signal of one frame is read out from the imaging unit via the analog-to-digital converter and the serial-parallel conversion unit, in addition to performing the alignment before a first analog-to-digital conversion period out of the plurality of analog-to-digital conversion periods.

7. The apparatus according to claim 1, wherein the alignment unit performs the alignment at least twice in a period during which a signal of one frame is read out from the imaging unit via the analog-to-digital converter and the serial-parallel conversion unit, in addition to performing the alignment before a first analog-to-digital conversion period out of the plurality of analog-to-digital conversion periods.

8. The apparatus according to claim 1, wherein the analog-to-digital converter includes an analog-to-digital conversion unit configured to convert the analog signals from the imaging unit into digital signals and a serializer configured to convert the digital signals from the analog-to-digital conversion unit into serial data.

9. The apparatus according to claim 1, further comprising a processing unit configured to process the parallel data from the serial-parallel conversion unit.

10. A radiation imaging system comprising:
a radiation source;
the radiation imaging apparatus according to claim 1;
a processor configured to generate image data for the radiation images of the plurality of frames based on signals for the radiation images of the plurality of frames from the apparatus; and
a display configured to display the radiation images of the plurality of frames based on the image data from the processor.

11. A control method of a radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the radiation imaging apparatus comprising
an imaging unit having a plurality of sensors configured to detect radiation, and configured to output an analog signal from each of the plurality of sensors,
an analog-to-digital converter configured to, in each of a plurality of analog-to-digital conversion periods corresponding to the plurality of frames, convert the individual analog signals from the imaging unit into individual digital signals and output the individual digital signals as a serial data string of a plurality of bits, and
a serial-parallel conversion unit configured to convert, into parallel data, the serial data string of the plurality of bits transmitted from the analog-to-digital converter via a transmission path,
the control method comprising performing alignment for the serial-parallel conversion unit to identify the serial data string of the plurality of bits such that the processor correctly receives the signals for the radiation images of the plurality of frames from the apparatus, wherein
in the performing the alignment, the alignment is performed in at least a period between, out of the plurality of analog-to-digital conversion periods, one analog-to-digital conversion period and another analog-to-digital conversion period.

12. A radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the apparatus comprising:
an imaging unit having a plurality of sensors configured to detect radiation, and configured to output an analog signal from each of the plurality of sensors;
an analog-to-digital converter including an analog-to-digital conversion circuit configured to, in each of a plurality of analog-to-digital conversion periods corresponding to the plurality of frames, convert the analog signals from the imaging unit into digital signals in accordance with a clock signal, an alignment pattern generator configured to generate digital signals of alignment patterns, and a circuit configured to select ones of the digital signals from the analog-to-digital conversion circuit and the digital signals from the alignment pattern generator and output, to a transmission path, selected digital signals as a serial data string of a plurality of bits and a serial clock in synchronism with the serial data string;
a serial-parallel conversion unit configured to convert, into parallel data, in accordance with the serial clock, the serial data string of the plurality of bits transmitted from the analog-to-digital converter via the transmission path;
an alignment pattern storage unit configured to store an alignment pattern used for alignment; and
an alignment unit configured to perform alignment for the serial-parallel conversion unit to identify the serial data string of the plurality of bits by comparing the serial data string of the plurality of bits including the alignment pattern generated by the alignment pattern generator with the alignment pattern stored in the alignment pattern storage unit such that the processor correctly receives the signals for the radiation images of the plurality of frames from the apparatus, wherein
the alignment unit performs the alignment in at least a period between, out of the plurality of analog-to-digital conversion periods, one analog-to-digital conversion period and another analog-to-digital conversion period.

13. A control method of a radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the radiation imaging apparatus comprising an imaging unit having a plurality of sensors configured to detect radiation, and configured to output an analog signal from each of the plurality of sensors;

an analog-to-digital converter including an analog-to-digital conversion circuit configured to, in each of a plurality of analog-to-digital conversion periods corresponding to the plurality of frames, convert the analog signals from the imaging unit into digital signals in accordance with a clock signal, an alignment pattern generator configured to generate digital signals of alignment patterns, and a circuit configured to select ones of the digital signals from the analog-to-digital conversion circuit and the digital signals from the alignment pattern generator and output, to a transmission path, selected digital signals as a serial data string of a plurality of bits and a serial clock in synchronism with the serial data string;

a serial-parallel conversion unit configured to convert, into parallel data, in accordance with the serial clock, the serial data string of the plurality of bits transmitted from the analog-to-digital converter via the transmission path; and an alignment pattern storage unit configured to store an alignment pattern used for alignment, the control method comprising performing alignment for the serial-parallel conversion unit to identify the serial data string of the plurality of bits by comparing the serial data string of the plurality of bits including the alignment pattern generated by the alignment pattern generator with the alignment pattern stored in the alignment pattern storage unit such that the processor correctly receives the signals for the radiation images of the plurality of frames from the apparatus, wherein in the performing the alignment, the alignment is performed in at least a period between, out of the plurality of analog-to-digital conversion periods, one analog-to-digital conversion period and another analog-to-digital conversion period.

14. A radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the apparatus comprising:

an imaging unit having a plurality of sensors configured to detect radiation, and configured to output an analog signal from each of the plurality of sensors;

an analog-to-digital converter configured to, in each of a plurality of analog-to-digital conversion periods corresponding to the plurality of frames, convert the individual analog signals from the imaging unit into individual digital signals and output the individual digital signals as a serial data string of a plurality of bits;

a serial-parallel conversion unit configured to convert, into parallel data, the serial data string of the plurality of bits transmitted from the analog-to-digital converter via a transmission path; and an alignment unit configured to perform alignment for the serial-parallel conversion unit to identify the serial data string of the plurality of bits such that the processor correctly receives the signals for the radiation images of the plurality of frames from the apparatus, wherein the alignment unit performs the alignment between a serial data string output during one analog-to-digital conversion period of the plurality of analog-to-digital conversion periods and a serial data string output during another analog-to-digital conversion period of the plurality of analog-to-digital conversion periods.

15. A radiation imaging system, comprising:

a radiation source;

the radiation imaging apparatus according to claim 14;

a processor configured to generate image data for the radiation images of the plurality of frames based on signals for the radiation images of the plurality of frames from the apparatus; and a display configured to display the radiation images of the plurality of frames based on the image data from the processor.

16. A control method of a radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the radiation imaging apparatus comprising:

an imaging unit having a plurality of sensors configured to detect radiation, and configured to output an analog signal from each of the plurality of sensors;

an analog-to-digital converter configured to, in each of a plurality of analog-to-digital conversion periods corresponding to the plurality of frames, convert the individual analog signals from the imaging unit into individual digital signals and output the individual digital signals as a serial data string of a plurality of bits; and a serial-parallel conversion unit configured to convert, into parallel data, the serial data string of the plurality of bits transmitted from the analog-to-digital converter via a transmission path;

the control method comprising performing alignment for the serial-parallel conversion unit to identify the serial data string of the plurality of bits such that the processor correctly receives the signals for the radiation images of the plurality of frames from the apparatus, wherein in the performing the alignment, the alignment is performed between a serial data string output during one analog-to-digital conversion period of the plurality of analog-to-digital conversion periods and a serial data string output during another analog-to-digital conversion period of the plurality of analog-to-digital conversion periods.

17. A radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the apparatus comprising:

an imaging unit having a plurality of sensors configured to detect radiation, and configured to output an analog signal from each of the plurality of sensors;

an analog-to-digital converter including an analog-to-digital conversion circuit configured to, in each of a plurality of analog-to-digital conversion periods corresponding to the plurality of frames, convert the analog signals from the imaging unit into digital signals in accordance with a clock signal, an alignment pattern generator configured to generate digital signals of alignment patterns, and a circuit configured to select ones of the digital signals from the analog-to-digital conversion circuit and the digital signals from the alignment pattern generator and output, to a transmission path, selected digital signals as a serial data string of a plurality of bits and a serial clock in synchronism with the serial data string;

a serial-parallel conversion unit configured to convert, into parallel data, in accordance with the serial clock, the serial data string of the plurality of bits transmitted from the analog-to-digital converter via the transmission path;

an alignment pattern storage unit configured to store an alignment pattern used for alignment; and an alignment unit configured to perform alignment for the serial-parallel conversion unit to identify the serial data string of the plurality of bits by comparing the serial data string of the plurality of bits including the alignment pattern generated by the alignment pattern generator with the alignment pattern stored in the alignment pattern storage unit such that the processor correctly receives the signals for the radiation images of the plurality of frames from the apparatus, wherein the alignment unit performs the alignment between a serial data string output during one analog-to-digital conversion period of the plurality of analog-to-digital conversion periods and a serial data string output during another analog-to-digital conversion period of the plurality of analog-to-digital conversion periods.

18. A control method of a radiation imaging apparatus which captures radiation images of a plurality of frames successively, the apparatus being used in a radiation imaging system composed of the apparatus, a processor configured to generate image data for the radiation images of the plurality of frames based on signals for the radiation images of the plurality of frames from the apparatus, and a display configured to display the radiation images of the plurality of frames based on the image data from the processor, the radiation imaging apparatus, comprising:

an imaging unit having a plurality of sensors configured to detect radiation, and configured to output an analog signal from each of the plurality of sensors;

an analog-to-digital converter including an analog-to-digital conversion circuit configured to, in each of a plurality of analog-to-digital conversion periods corresponding to the plurality of frames, convert the analog signals from the imaging unit into digital signals in accordance with a clock signal, an alignment pattern generator configured to generate digital signals of alignment patterns, and a circuit configured to select ones of the digital signals from the analog-to-digital conversion circuit and the digital signals from the alignment pattern generator and output, to a transmission path, selected digital signals as a serial data string of a plurality of bits and a serial clock in synchronism with the serial data string;

a serial-parallel conversion unit configured to convert, into parallel data, in accordance with the serial clock, the serial data string of the plurality of bits transmitted from the analog-to-digital converter via the transmission path; and an alignment pattern storage unit configured to store an alignment pattern used for alignment, the control method comprising performing alignment for the serial-parallel conversion unit to identify the serial data string of the plurality of bits by comparing the serial data string of the plurality of bits including the alignment pattern generated by the alignment pattern generator with the alignment pattern stored in the alignment pattern storage unit such that the processor correctly receives the signals for the radiation images of the plurality of frames from the apparatus, wherein in the performing the alignment, the alignment is performed between a serial data string output during one analog-to-digital conversion period of the plurality of analog-to-digital conversion periods and a serial data string output during another analog-to-digital conversion period of the plurality of analog-to-digital conversion periods.

* * * * *